(12) United States Patent
Liu et al.

(10) Patent No.: US 11,911,423 B2
(45) Date of Patent: Feb. 27, 2024

(54) BIFIDOBACTERIUM LACTIS BL-99 AND APPLICATION THEREOF

(71) Applicant: Inner Mongolia Yili Industrial Group Co., Ltd., Hohhot (CN)

(72) Inventors: Wei-Hsien Liu, Hohhot (CN); Wei-Lian Hung, Hohhot (CN); Ting Sun, Hohhot (CN); Wen Zhao, Hohhot (CN); Ignatius Man-Yau Szeto, Hohhot (CN)

(73) Assignee: Inner Mongolia Yili Industrial Group Co., Ltd., Hohhot (CN)

( * ) Notice: Subject to any disclaimer, the term of this patent is extended or adjusted under 35 U.S.C. 154(b) by 0 days.

(21) Appl. No.: 17/685,974

(22) Filed: Mar. 3, 2022

(65) Prior Publication Data

US 2022/0313755 A1    Oct. 6, 2022

Related U.S. Application Data

(60) Division of application No. 17/217,305, filed on Mar. 30, 2021, now Pat. No. 11,298,382, which is a continuation of application No. PCT/CN2019/107392, filed on Sep. 24, 2019.

(30) Foreign Application Priority Data

Sep. 30, 2018  (CN) .......................... 201811161053.6
Sep. 30, 2018  (CN) .......................... 201811161107.9
Sep. 30, 2018  (CN) .......................... 201811161108.3

(51) Int. Cl.
*A61K 35/745*    (2015.01)
*A23L 33/135*    (2016.01)

(52) U.S. Cl.
CPC .......... *A61K 35/745* (2013.01); *A23L 33/135* (2016.08)

(58) Field of Classification Search
None
See application file for complete search history.

(56) References Cited

U.S. PATENT DOCUMENTS

| | | | |
|---|---|---|---|
| 7,910,144 | B2 | 3/2011 | Ballevre et al. |
| 8,765,118 | B2 | 7/2014 | Garrigues et al. |
| 9,060,540 | B2 * | 6/2015 | Rochat ................. A61K 35/745 |
| 11,298,382 | B2 | 4/2022 | Liu et al. |
| 2012/0276143 | A1 | 11/2012 | O'Mahoney et al. |
| 2014/0248247 | A1 | 9/2014 | Bergonzelli Degonda et al. |
| 2021/0228656 | A1 | 7/2021 | Liu et al. |
| 2022/0313754 | A1 | 10/2022 | Liu et al. |

FOREIGN PATENT DOCUMENTS

| | | |
|---|---|---|
| CN | 102845518 A | 1/2013 |
| CN | 102946891 A | 2/2013 |
| CN | 103889241 A | 6/2014 |
| CN | 106072657 A | 11/2016 |
| CN | 106858605 A | 6/2017 |
| CN | 106962482 A | 7/2017 |
| CN | 108220193 A | 6/2018 |
| EP | 3048165 A1 | 7/2016 |
| WO | 00115715 A2 | 3/2001 |
| WO | 2018050623 A1 | 3/2018 |
| WO | 2020063553 A1 | 4/2020 |

OTHER PUBLICATIONS

Arunachalam et al. "Enhancement of natural immune function by dietary consumption of Bifidobacterium lactis (HN019)". European Journal of Clerical Nutrition. 2000, 54, pp. 263-267.*
Wang et al. "Fermented milk supplemented with probiotics and prebiotics can effectively alter the intestinal microbiota and immunity of host animals", J Dairy Sci., 2012, 95, pp. 4813-4822.*
Arunachalam, K., et al, "Enhancement of natural immune function by dietary consumption of Bi®dobacterium lactis" (HN019), European Journal of Clinical Nutrition, (2000) vol. 54, 263-267.
Brand of Yilixiao is Upgraded: the First Exclusive Probiotic "BL-99" Protects Intestinal Health) Baidu website, w/ translation (Aug. 6, 2019).
Cai, M., et al, "Animal studies on enhancement of immune function by dietary probiotic supplementation of Lactobacillus acidophilus NCFM and Bifidobacterium lactis Bi-07", Chinese Journal of Microecology vol. 20, No. 1 (2008).
Chen , S., "Application of Lactobacillus casei Zhang and Bifidobacterium lactis V9 in active lactobacillus drink", Food and fermentation industries, vol. 41, No. 11 (2015), 5 pgs.
Chen, K. et al., "Screening for highly adherent probiotic bacteria with the ability to degrade cholesterol", Food Science and Technology, vol. 43 No. 11 (2018).
Collins, F., et al., "The potential of probiotics as a therapy for osteoporosis", Microbiol Spectrum 5(4):BAD-0015-2016. doi:10.1128/microbiolspec.BAD-0015-2016 (2017).
Dar, H., et al, "Lactobacillus acidophilus inhibits bone loss and increases bone heterogeneity in osteoporotic mice via modulating Treg-Th17 cell balance", Bone Reports, 45-56 (2018).
Gao, P.,et al, "Screening and identification of probiotic Bifidobacterium from Mongolian children", Microbiologica Sinica, vol. 49, No. 2, 210-216 (Feb. 4, 2009).

(Continued)

*Primary Examiner* — Vera Afremova
(74) *Attorney, Agent, or Firm* — Hamilton, Brook, Smith & Reynolds, P.C.

(57) ABSTRACT

A *Bifidobacterium lactis* BL-99 strain capable of enhancing immunity and the use thereof, which belongs to the technical field of microorganisms, is described. The *Bifidobacterium lactis* BL-99 provided by the present invention is deposited in China General Microbiological Culture Collection Center CGMCC on Apr. 26, 2018 with the deposit number CGMCC No. 15650. The bacteria have gastric acid resistance and intestinal fluid resistance, can significantly promote the growth of *Bifidobacterium* and *Lactobacillus*, significantly increase antibody-producing cells and half hemolysis value $HC_{50}$, activate NK cell activity, and can be used to prepare foods for immunity enhancement. It also has the effects in preventing osteoporosis, increasing blood calcium and/or phosphorus ions, which has a wide range of application prospects.

15 Claims, 10 Drawing Sheets

Specification includes a Sequence Listing.

(56) References Cited

OTHER PUBLICATIONS

International Search Report for Application No. PCT/CN2019/107392, entitled "Bifidobacterium Lactis BL-99 and Application Thereof," dated Nov. 22, 2019 (with translation).
Jiang, X., et al., "The Safety Assessment of Animal Species of Lactobacillus BZ25)," The Food Industry, vol. 38, No. (1), (2017).
Jin, S., et al., "Study on evaluating the promote effect of danisco products on Bifidobacterium lactis Bi07 and lactobacillus acidophilus NCFM on physical intestinal canal microbial eco-system" Clin J. Dis Control Prev 2010,14 (2) :169-171.
Li, L, et al, "Gut microbiota and bone metabolism",Chin J Osteoprosis & Bone Miner Res,vol. 11 No. 3, May 10, 2018.
Studies on Selection, Physiological Characteristics and Application of an Aerolerant Bifidobacterium, Database (Medicine and Health Sciences, No. No. 8, Aug. 15, 2011, ISSN: 1674-022X (Aug. 15, 2011).
Li, Q., "Screening of Oxygen-tolerant Bifidobacterium and Its Physiological Characteristics and Application", Full-text database of Chinese doctoral dissertations (electronic journals), Aug. 15, 2011.
Miller, L.E., et al, "The Effect of *Bifidobacterium animalis* ssp. lactis HN019 on Cellular Immune Function in Healthy Elderly Subjects Systematic Review and Meta-Analysis", Nutrients 2017, 9, 191.
Parvaneh, K.,et al, "Probiotics (Bifidobacterium longum) Increase Bone Mass Density and Upregulate Sparc and Bmp-2 Genes in Rats with Bone Loss Resulting from Ovariectomy", BioMed Research International, (2015), 10 pgs.
Wang, H., "The research of functional properties of Bifidobacterium BB12 fermented milk", China Excellent Master's Thesis Full-text Database, Jun. 2009.
Yang, H et al, "Research on in vivo Immunostimulation Function of Bifidobacterium Strain BBMN01", Food Science and Technology, vol. 29, No. 2, 369-372 (2008).
Detection of antimicrobial resistance of the bacteria in animal and animal products—Disk diffusion testing, SN/T 1944-2007 (Mar. 1, 2008).
Li, Qingqing et al: "Isolation and characterisation of an oxygen, acid and bile resistant *Bifidobacterium animalis* subsp. lactis Qq08", Journal of the Science of Food and Agriculture,vol. 90, No. 8, Apr. 14, 2010 pp. 1340-1346.
Jungersen Mikkel et al: "The Science behind the Probiotic Strain *Bifidobacterium animalis* subsp. Lactis BB-12" Microorganisms, vol. 2, No. 2, Mar. 28, 2014, pp. 92-110.
European Supplementary Search Report for EP Application No. 9867197.6 "Bifidobacterium Lactis BL-99 and Application Thereof" dated Oct. 1, 2021.
Ashraf et al. "Commercial lactic acid bacteria and probiotic stains tolerance to bile, pepsin and antibiotics". International Food Research Journal. 2016, 23(2), pp. 777-789.
Non-Final Office Action for U.S. Appl. No. 17/217,305, "Bifidobacterium Lactis BL-99 and Application Thereof", consisting of 16 pages, dated Aug. 20, 2021.
Notice of Allowance for U.S. Appl. No. 17/217,305, "Bifidobacterium Lactis BL-99 and Application Thereof", consisting of 12 pages, dated Dec. 3, 2021.
International Preliminary Report on Patentability and Written Opinion for International Application No. PCT/CN2019/107392, entitled "Bifidobacterium Lactis BL-99 and Application Thereof," dated Mar. 23, 2021 (with English Translation).
Non-Final Office Action for U.S. Appl. No. 17/685,908, "Bifidobacterium Lactis BL-99 and Application Thereof" dated Jun. 14, 2023.

\* cited by examiner

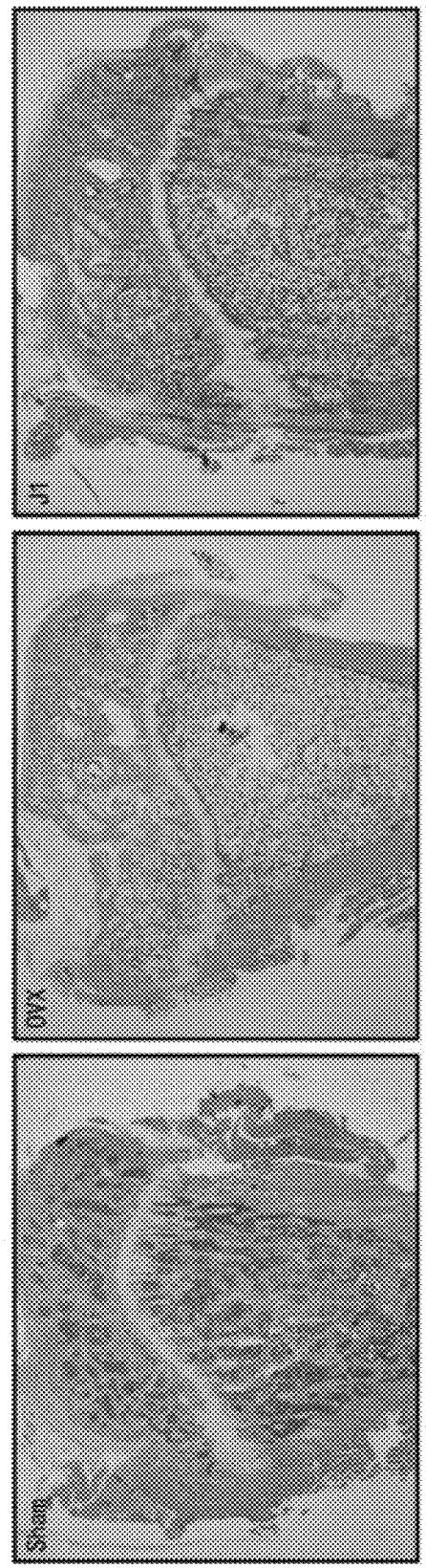
FIG. 2A Sham operation
FIG. 2B ovariectomy
FIG. 2C ovariectomy

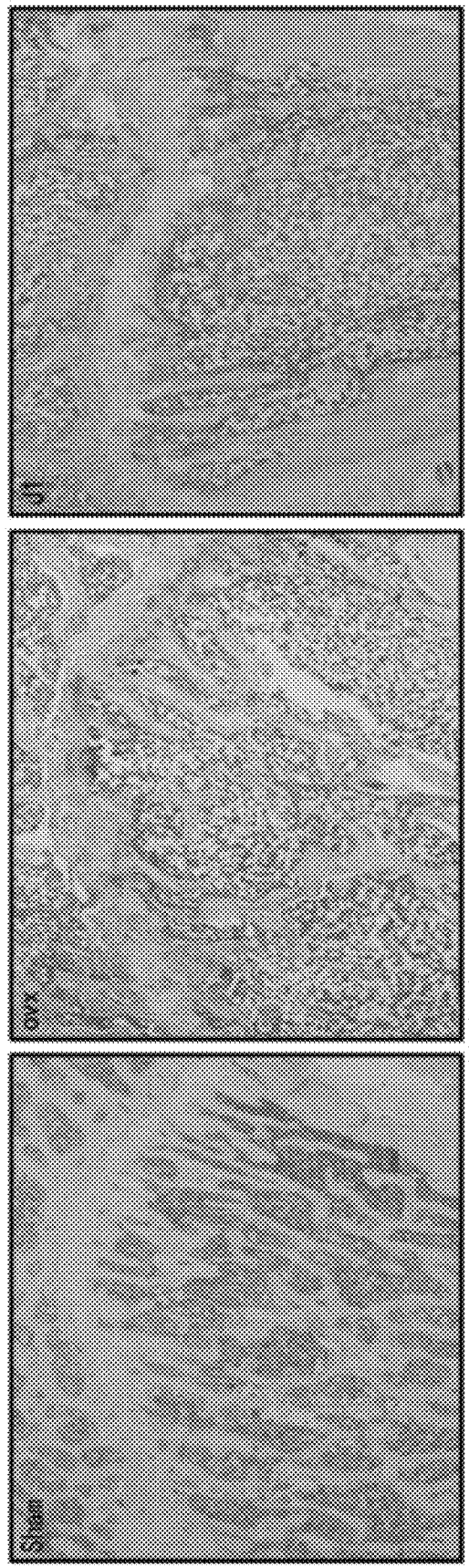
FIG. 3A Sham operation
FIG. 3B ovariectomy
FIG. 3C ovariectomy+BL99

SEQUENCE LISTING

<160> NUMBER OF SEQ ID NOS: 11

<210> SEQ ID NO 1
<211> LENGTH: 1398
<212> TYPE: DNA
<213> ORGANISM: Bifidobacterium lactis

<400> SEQUENCE: 1
gctcccccac aagggtcggg ccaccggctt cgggtgctac ccactttcat gacttgacgg      60
gcggtgtgta caaggcccgg gaacgcattc accgcggcgt tgctgatccg cgattactag     120

```
cgactccgcc ttcacgcagt cgagttgcag actgcgatcc gaactgagac cggttttcag    180
cgatccgccc cacgtcaccg tgtcgcaccg cgttgtaccg gccattgtag catgcgtgaa    240
gccctggacg taaggggcat gatgatctga cgtcatcccc accttcctcc gagttgaccc    300
cggcggtccc acatgagttc ccggcatcac ccgctggcaa catgcggcga gggttgcgct    360
cgttgcggga cttaacccaa catctcacga cacgagctga cgacgaccat gcaccacctg    420
tgaaccggcc ccgaagggaa accgtgtctc cacggcgatc cggcacatgt caagcccagg    480
taaggttctt cgcgttgcat cgaattaatc cgcatgctcc gccgcttgtg cgggcccccg    540
tcaatttctt tgagttttag ccttgcggcc gtactcccca ggcgggatgc ttaacgcgtt    600
ggctccgaca cgggacccgt ggaaagggcc ccacatccag catccaccgt ttacggcgtg    660
gactaccagg gtatctaatc ctgttcgctc cccacgcttt cgctcctcag cgtcagtgac    720 gcccagaga cctgccttcg ccattggtgt tcttcccgat atctacacat tccaccgtta    780
caccgggaat ccagtctcc cctaccgcac tccagcccgc ccgtaccgg cgcagatcca    840 ccgttaggcg atggactttc acaccggacg cgacgaaccg cctacgagcc ctttacgccc    900
aataaatccg gataacgctc gcaccctacg tattaccgcg gctgctggca cgtagttagc    960
cggtgcttat tcgaacaatc cactcaacac ggccgaaacc gtgccttgcc cttgaacaaa   1020
agcggtttac aacccgaagg cctccatccc gcacgcggcg tcgctgcatc aggcttgcgc   1080
ccattgtgca atattcccca ctgctgcctc ccgtaggagt ctgggccgta tctcagtccc   1140
aatgtggccg gtcaccctct caggccggct accgtcaac gccttggtgg gccatcaccc   1200
cgccaacaag ctgataggac gcgaccccat cccatgccgc aaaagcattt cccacccac   1260 catgcgatgg agcggagcat ccggtattac caccgtttc caggagctat tccggtgcac   1320
agggcaggtt ggtcacgcat tactcacccg ttcgccactc tcaccccgac agcaagctgc   1380
cagggatccc gttcgact                                                 1398
```

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gcaaggacat cgcctatcag                                                 20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
agttcagtgc ggttccagac                                                 20

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4

```
cacagggagg tgtgtgag                                                    18

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
tgtgccgtcc atactttc                                                    18

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gttcttgcac agcttcacca                                                  20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
aaacagccca gtgaccattc                                                  20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
catcgggttc ccataaagtc                                                  20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ctgaagcaaa tgttggcgta                                                  20

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
agtctactgg cgtcttcac                                                   19

<210> SEQ ID NO 11
<211> LENGTH: 20
<212> TYPE: DNA
<213> ORGANISM: Artificial Sequence
```

```
<220> FEATURE:
<223> OTHER INFORMATION: primer

<400> SEQUENCE: 11
tcatatttct cgtggttcac                                                   20
```

BIFIDOBACTERIUM LACTIS BL-99 AND APPLICATION THEREOF

CROSS-REFERENCE TO RELATED APPLICATIONS

This application is a divisional of U.S. application Ser. No. 17/217,305, filed on Mar. 30, 2021, which is a continuation of International Application No. PCT/CN2019/107392, which designated the United States and was filed on Sep. 24, 2019, published in Chinese and claims priority under 35 U.S.C. § 119 or 365 to Chinese Patent Application No. 201811161108.3, filed on Sep. 30, 2018, Chinese Patent Application No. 201811161053.6, filed on Sep. 30, 2018 and Chinese Patent Application No. 201811161107.9, filed on Sep. 30, 2018. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
  a) File name: 58981001005_SEQUENCELISTING.txt; created Feb. 25, 2022, 4,291 Bytes in size.

TECHNICAL FIELD

The present invention relates to the field of microbial technology, in particular to a *Bifidobacterium lactis* strain having gastric acid resistance and intestinal fluid resistance which can significantly promote the growth of *Bifidobacterium* and *Lactobacillus* and has immunomodulatory activity as well as effects in preventing osteoporosis and increasing blood calcium and/or phosphorus ions.

BACKGROUND

Studies have shown that probiotics such as *Bifidobacterium lactis* have various functions, such as regulating intestinal disorders, enhancing intestinal immune function, and inhibiting allergic reactions. The World Health Organization defines a probiotic product as a food containing live microorganisms in a sufficient amount that can maintain an appropriate number of viable bacteria and bacterial activity even after being subjected to various processes in food processing and entering the human intestine. Therefore, it is generally considered necessary for a strain to maintain a relatively stable number of viable bacteria to be able to maintain a relatively stable number of viable bacteria after the bacteria powder is prepared and the product is produced and processed and withstands the gastric acid and bile salt stress in the human gastrointestinal tract.

However, acid intolerance and gastrointestinal fluid intolerance are common properties of *Bifidobacterium*, which makes it difficult to pass through gastric juice to reach the intestine and colonize in the intestine. Therefore, screening of *Bifidobacterium* probiotics with gastric acid resistance and intestinal fluid resistance is an important research direction in the field.

SUMMARY

An object of the present invention is to provide a new *Bifidobacterium lactis* strain and the use thereof.

In one aspect, the present invention provides a *Bifidobacterium lactis* strain with gastric acid resistance which has a survival rate of viable bacteria of 62% or more when treated in gastric acid at pH 2.5 for 30 minutes, and a survival rate of viable bacteria of 61% or more when treated for 2 hours. The *Bifidobacterium lactis* strain provided by the present invention also has intestinal fluid resistance and a survival rate of viable bacteria of 70% or more when treated in small intestinal fluid at pH 6.8 for 2 hours. The *Bifidobacterium lactis* strain provided by the present invention is designated as BL-99. This strain has been deposited on Apr. 26, 2018 in China General Microbiological Culture Collection Center CGMCC (Address: No. 3, Square 1, West Beichen Road, Chaoyang District, Beijing, Institute of Microbiology, Chinese Academy of Sciences), taxonomic designation: *Bifidobacterium lactis*; deposit number: CGMCC No. 15650.

It is discovered in the present invention that the *Bifidobacterium lactis* BL-99 strain (i.e., the *Bifidobacterium lactis* strain with the deposit number CGMCC No. 15650) of the present invention is capable of significantly promoting the growth of intestinal *Bifidobacterium* and *Lactobacillus*, inhibiting the growth of *Desulfovibrio* and/or *Enterobacter* in the intestine, and in particular therapeutically inhibiting the growth of *Helicobacter* and/or *Escherichia-Shigella*, and it has a prominent effect in regulating gastrointestinal flora.

In addition, the *Bifidobacterium lactis* BL-99 strain (i.e., the *Bifidobacterium lactis* strain with the deposit number CGMCC No. 15650) of the present invention can be used to enhance the immune response of the body, and to improve the immune system disorders caused by irregular diet and increased work pressure, specifically including: (1) increasing the carbon clearance index of mice; (2) increasing the half hemolysis value of mice; (3) increasing the number of antibody-producing cells of mice; (4) activating NK cell activity; (5) positive delayed immune response; (6) increasing macrophage phagocytosis rate and phagocytosis index.

Further, it is discovered in the present invention that the *Bifidobacterium lactis* BL-99 strain according to the present invention can be used to treat or prevent osteoporosis (few reports in the prior art were about the use of *Bifidobacterium lactis* in treating and/or preventing osteoporosis), and is effective in increasing blood calcium ion and/or phosphorus ion concentration, specifically including: (1) significantly reducing the loss of bone mass caused by estrogen deficiency; (2) increasing blood calcium ion and phosphorus ion concentration; (3) inhibiting the number of osteoclasts in the body and inhibiting their bone resorption by adjusting the OPG/RANKL ratio; (4) increasing the level of the expression protein of the bone anabolism related factor gene, such as alkaline phosphatase and osteocalcin, by promoting the expression of the protein so as to promote the formation of new bones.

*Bifidobacterium lactis* BL-99 of the present invention can be cultured by anaerobic fermentation in a *Bifidobacterium lactis* culture medium (e.g., TPY medium, BBL medium and the like) commonly used in the field. The best fermentation temperature is 35 to 38° C., and the best fermentation duration is 7 to 24 h. The present invention also provides a preparation method of a *Bifidobacterium lactis* BL-99 bacteria preparation, comprising anaerobic culturing the strain in a liquid fermentation medium to obtain a bacteria-containing fermentation broth. The fermentation broth may be used directly or further concentrated as a liquid bacteria preparation. Also, the fermentation broth may be dried to prepare a bacteria powder, or the bacteria is isolated from the fermentation broth to prepare a bacteria powder. The liquid bacteria preparation of the present invention may also be a liquid preparation obtained by resuspending the bacteria in a solvent such as a culture medium, a buffer solution, or deionized water. The BL-99 liquid bacteria preparation or solid bacteria preparation (bacteria powder) according to the present invention may be stored in a viable bacteria form and has good stability over the storage period. The BL-99 liquid bacteria preparation or solid bacteria preparation (bacteria powder) according to the present invention may also be stored in a form of inactivated non-viable bacteria. The bacteria preparation can be used in the production of foods, feeds or pharmaceutics. Experiments in mice show that the strain has no acute oral toxicity, no antibiotic resistance, and is safe in food processing.

Therefore, in one aspect, the present invention provides a *Bifidobacterium lactis* strain with the deposit number CGMCC No. 15650.

In another aspect, the present invention also provides a bacteria preparation of *Bifidobacterium lactis* containing the *Bifidobacterium lactis* strain according to the present invention, which is a solid or liquid bacteria preparation. The bacteria preparation of *Bifidobacterium lactis* according to the present invention may be in a viable bacteria form or an inactivated form.

In another aspect, the present invention also provides the use of the *Bifidobacterium lactis* strain or the bacteria preparation of *Bifidobacterium lactis* in the preparation of a composition effective in regulating intestinal flora. The composition includes a food composition, a feed composition, or a pharmaceutical composition.

In another aspect, the present invention also provides the use of the *Bifidobacterium lactis* strain or the bacteria preparation of *Bifidobacterium lactis* in the preparation of a composition effective in increasing the number of *Bifidobacterium* and/or *Lactobacillus* in the intestine. The composition includes a food composition, a feed composition, or a pharmaceutical composition.

In another aspect, the present invention also provides the use of the *Bifidobacterium lactis* strain or the bacteria preparation of *Bifidobacterium lactis* in the preparation of a composition effective in inhibiting *Desulfovibrio* and/or *Enterorhabdus* in the intestine. The composition includes a food composition, a feed composition, or a pharmaceutical composition.

In another aspect, the present invention also provides the use of the *Bifidobacterium lactis* strain or the bacteria preparation of *Bifidobacterium lactis* in the preparation of a composition effective in inhibiting *Helicobacter* and/or *Escherichia-Shigella*. The composition includes a food composition, a feed composition, or a pharmaceutical composition.

In another aspect, the present invention also provides the use of the *Bifidobacterium lactis* strain or the bacteria preparation of *Bifidobacterium lactis* in the preparation of a composition for improving the immunity activity of the body. The composition includes a food composition, a feed composition, or a pharmaceutical composition.

In another aspect, the present invention also provides the use of the *Bifidobacterium lactis* strain or the bacteria preparation of *Bifidobacterium lactis* in the preparation of a composition for improving the carbon clearance index of the body. The composition includes a food composition, a feed composition, or a pharmaceutical composition.

In another aspect, the present invention also provides the use of the *Bifidobacterium lactis* strain or the bacteria preparation of *Bifidobacterium lactis* in the preparation of a composition for improving the half hemolysis value of the body. The composition includes a food composition, a feed composition, or a pharmaceutical composition.

In another aspect, the present invention also provides the use of the *Bifidobacterium lactis* strain or the bacteria preparation of *Bifidobacterium lactis* in the preparation of a composition for increasing the number of antibody-producing cells of the body. The composition includes a food composition, a feed composition, or a pharmaceutical composition.

In another aspect, the present invention also provides the use of the *Bifidobacterium lactis* strain or the bacteria preparation of *Bifidobacterium lactis* in the preparation of a composition for activating the NK cell activity of the body. The composition includes a food composition, a feed composition, or a pharmaceutical composition.

In another aspect, the present invention also provides the use of the *Bifidobacterium lactis* strain or the bacteria preparation of *Bifidobacterium lactis* in the preparation of a composition for increasing the macrophage phagocytosis rate and phagocytosis index of the body. The composition includes a food composition, a feed composition, or a pharmaceutical composition.

In another aspect, the present invention also provides the use of the *Bifidobacterium lactis* strain or the bacteria preparation of *Bifidobacterium lactis* in the preparation of a composition for preventing and treating osteoporosis. The composition includes a food composition, a feed composition, or a pharmaceutical composition.

In another aspect, the present invention also provides the use of the *Bifidobacterium lactis* strain or the bacteria preparation of *Bifidobacterium lactis* in the preparation of a composition for reducing bone mass caused by estrogen deficiency. The composition includes a food composition, a feed composition, or a pharmaceutical composition.

In another aspect, the present invention also provides the use of the *Bifidobacterium lactis* strain or the bacteria preparation of *Bifidobacterium lactis* in the preparation of a composition for increasing blood calcium and/or blood phosphorus. The composition includes a food composition, a feed composition, or a pharmaceutical composition.

In another aspect, the present invention also provides the use of the *Bifidobacterium lactis* strain or the bacteria preparation of *Bifidobacterium lactis* in the preparation of a composition for inhibiting the number of osteoclasts in the body. The composition includes a food composition, a feed composition, or a pharmaceutical composition.

In another aspect, the present invention also provides the use of the *Bifidobacterium lactis* strain or the bacteria preparation of *Bifidobacterium lactis* in the preparation of a composition for promoting the expression protein of the bone anabolism-related factor gene. The composition includes a food composition, a feed composition, or a pharmaceutical composition. Specifically, the expressed protein of the bone anabolism-related factor gene includes alkaline phosphatase and/or osteocalcin and the like.

The composition of the present invention can be used in animals or human. The composition may also include conventional materials and components in the related field. For example, for a pharmaceutical composition, an appropriate amount of adjuvants may be included, and the adjuvants may be excipients, diluents, fillers, absorption enhancers and the like. For a food composition, the *Bifidobacterium lactis* strain according to the present invention may be produced in accordance with a *Bifidobacterium lactis*-containing food in the prior art, and the composition can adopt different forms according to the needs of the recipient, for example, powder, lozenge, granulation, microcapsule, liquid preparation and the like.

In some specific embodiments of the present invention, the present invention also provides a food comprising the *Bifidobacterium lactis* strain or the bacteria preparation of *Bifidobacterium lactis*; preferably, the food is a fermented dairy product (for example, fermented milk, flavored fermented milk, a fermented milk beverage, etc.), cheese, a dairy beverage, a solid beverage or milk powder. For the specific formula and production method of the food, reference can be made to those of the *Bifidobacterium lactis*-containing food in the prior art.

In some other specific embodiments of the present invention, the present invention also provides a medicament comprising the *Bifidobacterium lactis* strain or the bacteria preparation of *Bifidobacterium lactis*. For the specific formulation and production method of the medicament, reference can be made to those of the *Bifidobacterium lactis*-containing medicament in the prior art.

In some other specific embodiments of the present invention, the present invention also provides a feed comprising the *Bifidobacterium lactis* strain or the bacteria preparation of *Bifidobacterium lactis*. For the specific formula and production method of the feed, reference can be made to those of the probiotics-containing feed in the prior art, provided that the *Bifidobacterium lactis* strain or the bacteria preparation according to the present invention may be added as a probiotic supplement.

Preferably, in the food, medicament, or feed, the recommended dosage of the *Bifidobacterium lactis* BL-99 for animals or human may be $1.0 \times 10^3$ CFU to $1.0 \times 10^{10}$ CFU/kg body weight/day. Alternatively, in the food, medicament, or feed, the recommended dosage of *Bifidobacterium lactis* BL-99 for animals or human may be 0.001 μg to 100 mg/kg body weight/day, more preferably 0.01 μg to 10 mg/kg body weight/day. The food, medicament, or feed according to the present invention have the corresponding potency of regulating the gastrointestinal flora, enhancing immunity, and/or preventing osteoporosis due to the *Bifidobacterium lactis* BL-99 strain comprised therein.

In another aspect, the present invention also provides a method for regulating the gastrointestinal flora, comprising administering an effective amount of the *Bifidobacterium lactis* strain BL-99 or the bacteria preparation of *Bifidobacterium lactis* according to the present invention to a subject. Specifically, the regulation of the gastrointestinal flora includes: increasing the number of *Bifidobacterium* and/or *Lactobacillus* in the intestine, inhibiting *Desulfovibrio* and/or *Enterorhabdus* in the intestine, and/or inhibiting *Helicobacter* and/or *Escherichia-Shigella*.

In another aspect, the present invention also provides a method for improving the immunity activity of the body, comprising administering the *Bifidobacterium lactis* strain BL-99 or the bacteria preparation of *Bifidobacterium lactis* according to the present invention to a subject. Specifically, improving the immunity activity of the body includes: increasing the carbon clearance index of the body, increasing the half hemolysis value of the body, increasing the antibody-producing cell number of the body, activating the NK cell activity of the body, and/or increasing the phagocytosis rate and phagocytosis index of macrophages in the body.

In another aspect, the present invention also provides a method for preventing and/or treating osteoporosis, comprising administering the *Bifidobacterium lactis* BL-99 strain or the bacteria preparation of *Bifidobacterium lactis* according to the present invention to a subject. Specifically, the prevention and/or treatment of osteoporosis includes: reducing bone loss caused by estrogen deficiency, increasing blood calcium and/or blood phosphorus, inhibiting the number of osteoclasts in the body, and/or promoting the expression protein of the bone anabolism-related factor gene. Preferably, the expressed protein of the bone anabolism-related factor gene includes alkaline phosphatase and/or osteocalcin.

In summary, the present invention provides a *Bifidobacterium lactis* BL-99 strain, which is the *Bifidobacterium lactis* with the deposit number CGMCC No. 15650. The *Bifidobacterium lactis* strain has gastric acid resistance and intestinal fluid resistance, and has the potency of regulating the gastrointestinal flora. Particularly, it can inhibit *Desulfovibrio* and/or *Enterobacter* in the intestine, and therapeutically inhibit *Helicobacter* and/or *Escherichia-Shigella*, and can be used to prepare foods, medicaments, and feeds that regulates the intestinal flora. In addition, this bacteria has the ability to enhance humoral immunity and activate NK cells, and can be used to improve problems such as compromised immunity due to irregular diet and increased working pressure. In addition, the bacteria has a significant efficacy of preventing and treating osteoporosis. The bacteria can be used for food, feed or medical purposes, and has a wide range of application prospects.

DESCRIPTION OF DRAWINGS

FIGS. 2A-2C show the results of HE staining in Example 4.

FIGS. 3A-3C show the results of TRAP staining of tibia in Example 4.

DEPOSIT OF MICROORGANISMS UNDER THE BUDAPEST TREATY

Figures 1A, 1B:
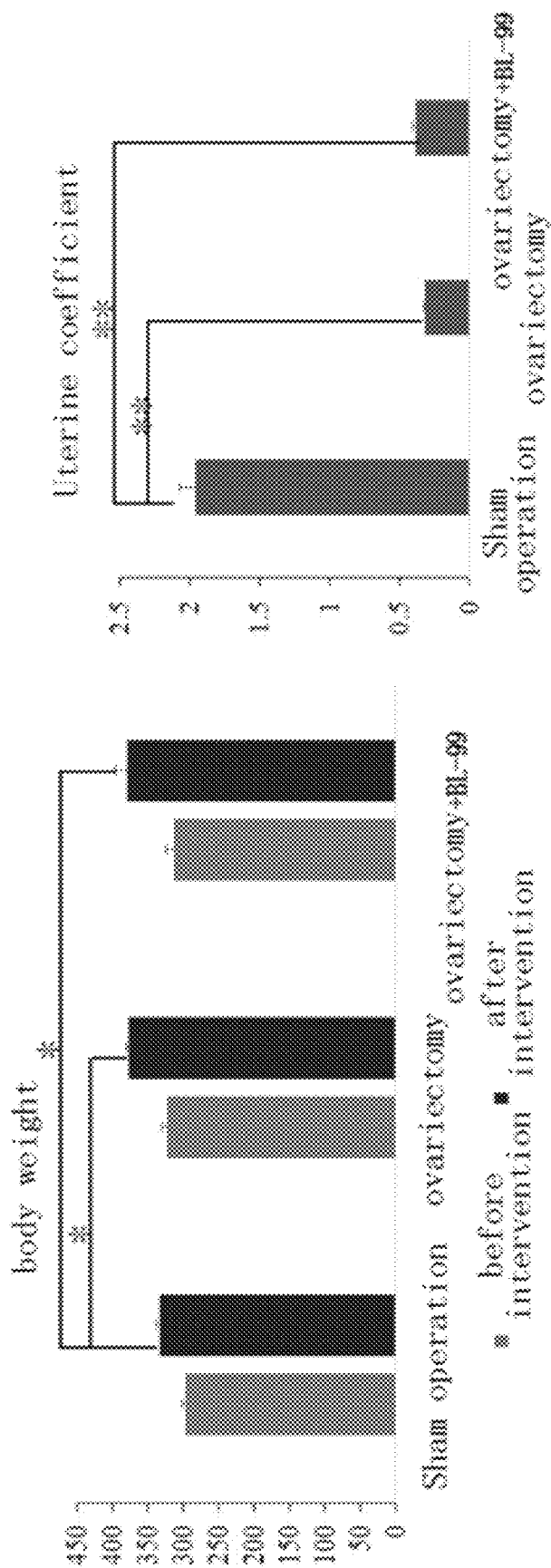
FIG. 1A shows the changes in body weight of the animals before and after the *Bifidobacterium lactis* BL-99 intervention in Example 4.
FIG. 1B shows the changes in the weight of the uterus of the animals before and after the *Bifidobacterium lactis* BL-99 intervention in Example 4.

*Bifidobacterium lactis* BL-99 according to the present invention:

Date of deposit: Apr. 26, 2018;

Depositary Authority: China General Microbiological Culture Collection Center CGMCC Address of the Depositary Authority: No. 3, Squre 1, West Beichen Road, Chaoyang District, Beijing, Institute of Microbiology, Chinese Academy of Sciences;

Deposit number: CGMCC No. 15650;

Taxonomic designation: *Bifidobacterium lactis*.

DETAILED DESCRIPTION OF INVENTION

For better understanding of the technical features, the purpose, and advantageous effects of the present invention, the technical solutions of the present invention are now described in detail in connection with specific examples. It should be understood that these examples are only used to illustrate the present invention, but not to limit the scope of the present invention. In the examples, the starting reagents and materials are commercially available, and the experimental methods without specified conditions are conventional methods and conventional conditions well known in the art, or in accordance with the conditions recommended by the instrument manufacturer.

Unless specifically defined otherwise, all technical and scientific terms used herein have the same meaning as those of ordinary skill in the relevant art commonly understand. Unless otherwise specified, all numbers used in the present invention indicating the amounts of ingredients, cell culture, processing conditions and the like should be understood as being modified by the term "about" under all circumstances. Therefore, unless otherwise stated, the numerical parameters are approximate values and may vary according to the desired characteristics intended to obtain by the present invention. Unless otherwise stated, the term "at least" preceding a series of elements should be construed as referring to each element in the series.

In each example of the present invention, the experimental data is expressed as Mean±S.E.M. The data is calculated by PRISM version 5.0 (GraphPad, San Diego, CA, USA). Differences between groups are calculated by one-way ANOVA followed by Tukery's multiple comparison test. A significant statistical difference is present at $P<0.05$.

Example 1: *Bifidobacterium lactis* BL-99 and its Performance Measurement

The *Bifidobacterium lactis* BL-99 of the present invention was obtained from Shanghai Jiao Da University Onlly Co., Ltd. as isolated from the intestinal tract of infants. This strain has been deposited in China General Microbiological Culture Collection Center CGMCC on Apr. 26, 2018 (address: No. 3, Square 1, West Beichen Road, Chaoyang District, Beijing, Institute of Microbiology, Chinese Academy of Sciences), taxonomic designation: *Bifidobacterium lactis*; deposit number: CGMCC No. 15650.

Taxonomic characteristics of *Bifidobacterium lactis* BL-99

Physical and Chemical Test Results

| Test Item | Result |
|---|---|
| Gram staining | positive |
| Cell shape | rod-shaped, polymorphic |
| Spore formation | – |
| Contact enzyme | – |
| Oxidase | – |
| Aerobic (air) growth | – |
| Anaerobic growth | + |
| Carbohydrate acid production | |
| Mannose | – |
| Melezitose | – |
| Fructose | – |
| Salicin | + |
| Inulin | – |
| Cellobiose | – |
| Starch | + |
| Ribose | + |
| Trehalose | – |
| Xylose | + |
| Maltose | + |
| Lactose | + |
| Raffinose | + |
| Sorbitol | – |
| Melibiose | + |
| Galactose | + |
| Mannitol | – |
| L-arabinose | – |
| Sodium gluconate | – |
| Sucrose | + |

Sequencing results of the 16S rRNA gene sequence (SEQ ID No. 1):
GCTCCCCACAAGGGTCGGGCCACCGGCTTCGGGTGCTACCCACTTTCA

TGACTTGACGGGCGGTGTGTACAAGGCCCGGGAACGCATTCACCGCGGC

GTTGCTGATCCGCGATTACTAGCGACTCCGCCTTCACGCAGTCGAGTTG

CAGACTGCGATCCGAACTGAGACCGGTTTTCAGCGATCCGCCCCACGTC

ACCGTGTCGCACCGCGTTGTACCGGCCATTGTAGCATGCGTGAAGCCCT

GGACGTAAGGGGCATGATGATCTGACGTCATCCCCACCTTCCTCCGAGT

TGACCCCGGCGGTCCCACATGAGTTCCCGGCATCACCCGCTGGCAACAT

GCGGCGAGGGTTGCGCTCGTTGCGGGACTTAACCCAACATCTCACGACA

CGAGCTGACGACGACCATGCACCACCTGTGAACCGGCCCCGAAGGGAAA

CCGTGTCTCCACGGCGATCCGGCACATGTCAAGCCCAGGTAAGGTTCTT

CGCGTTGCATCGAATTAATCCGCATGCTCCGCCGCTTGTGCGGGCCCCC

GTCAATTTCTTTGAGTTTTAGCCTTGCGGCCGTACTCCCCAGGCGGGAT

GCTTAACGCGTTGGCTCCGACACGGGACCCGTGGAAAGGGCCCCACATC

CAGCATCCACCGTTTACGGCGTGGACTACCAGGGTATCTAATCCTGTTC

GCTCCCCACGCTTTCGCTCCTCAGCGTCAGTGACGGCCCAGAGACCTGC

CTTCGCCATTGGTGTTCTTCCCGATATCTACACATTCCACCGTTACACC

GGGAATTCCAGTCTCCCCTACCGCACTCCAGCCCGCCCGTACCCGGCGC

AGATCCACCGTTAGGCGATGGACTTTCACACCGGACGCGACGAACCGCC

TACGAGCCCTTTACGCCCAATAAATCCGGATAACGCTCGCACCCTACGT

ATTACCGCGGCTGCTGGCACGTAGTTAGCCGGTGCTTATTCGAACAATC

CACTCAACACGGCCGAAACCGTGCCTTGCCCTTGAACAAAAGCGGTTTA

CAACCCGAAGGCCTCCATCCCGCACGCGGCGTCGCTGCATCAGGCTTGC

GCCCATTGTGCAATATTCCCCACTGCTGCCTCCCGTAGGAGTCTGGGCC

```
                        -continued
GTATCTCAGTCCCAATGTGGCCGGTCACCCTCTCAGGCCGGCTACCCGT

CAACGCCTTGGTGGGCCATCACCCCGCCAACAAGCTGATAGGACGCGAC

CCCATCCCATGCCGCAAAAGCATTTCCCACCCCACCATGCGATGGAGCG

GAGCATCCGGTATTACCACCCGTTTCCAGGAGCTATTCCGGTGCACAGG

GCAGGTTGGTCACGCATTACTCACCCGTTCGCCACTCTCACCCCGACAG

CAAGCTGCCAGGGATCCCGTTCGACT
```

2. Artificial Gastric Juice and Intestinal Fluid Resistance of *Bifidobacterium lactis* BL-99

*Bifidobacterium* is a bacteria genus generally non-resistant to acid. In this example, the artificial gastric juice and intestinal fluid resistance of the *Bifidobacterium lactis* BL-99 strain according to the present invention were tested. In addition, *Bifidobacterium lactis* BB-12®, which is well recognized in the art as having excellent acid resistance and being able to survive through the gastrointestinal tract, is used for comparison.

Test method: after culturing in MRS liquid medium at 37° C. for 16 hours, the *Bifidobacterium lactis* BL-99 strain was centrifuged at 4° C. and 2500 rpm for 10 minutes, followed by collection of the bacteria.

The strain to be tested was cultured in artificial gastric juice and artificial small intestinal fluid, respectively, and treated at 37° C. for 0 min, 30 min, and 2 h before the viable bacteria were counted and analyzed. The survival rate was used to evaluate the acid resistance and intestinal fluid resistance of the strain. Survival rate=(number of viable bacteria after treatment/number of viable bacteria at 0 min)× 100%.

The test results of the survival rate of the strains in artificial gastric acid (pH 2.5) are shown in Table 1. BB-12 had a survival rate of viable bacteria of 7.04% after being treated in artificial gastric acid (pH 2.5) for 30 minutes, and a survival rate of viable bacteria of only 1.64% after 2 h treatment; whereas, the *Bifidobacterium lactis* BL-99 according to the present invention had a survival rate of viable bacteria of 62.60% after being treated in artificial gastric acid (pH 2.5) for 30 minutes, and a survival rate of viable bacteria of 61.83% after 2 h treatment. This indicates that the *Bifidobacterium lactis* BL-99 according to the present invention has excellent gastric acid resistance and can pass through the stomach more smoothly into the intestine to exert a probiotic effect.

TABLE 1

| | Survival rate under challenge of artificial gastric acid (pH 2.5) | | |
|---|---|---|---|
| | Log CFU/ml (Survival percentage, %) | | |
| Strains | 0 min | 30 min | 2 h |
| BB-12 | 8.78 (100) | 7.63 (7.04) | 7 (1.64) |
| BL-99 | 9.42 (100) | 9.21 (62.60) | 9.21 (61.83) |

The test results of the survival rate of the strains in artificial small intestinal fluids (pH6.8) are shown in table 2. The data shows that BB-12 had a survival rate of viable bacteria of only 28.95% after being treated in artificial small intestinal fluid (pH6.8) for 2 hours; whereas, the *Bifidobacterium lactis* BL-99 according to the present invention had a survival rate of viable bacteria of 70.23% after being treated in artificial small intestinal fluid (pH6.8) for 2 hours. This indicates that the *Bifidobacterium lactis* BL-99 according to the present invention has excellent intestinal fluid resistance and can survive and colonize in the intestinal tract.

TABLE 2

| | Survival rate under challenge of artificial small intestinal fluid (pH 6.8) | |
|---|---|---|
| | Log CFU/ml (Survival percentage, %) | |
| Strains | 0 min | 2 h |
| BB-12 | 8.78 (100) | 8.24 (28.95) |
| BL-99 | 9.42 (100) | 9.26 (70.23) |

3. Virulence Test and Safety Test of *Bifidobacterium lactis* BL-99

The *Bifidobacterium lactis* BL-99 of the present invention was inoculated into a BBL liquid medium and cultured anaerobically at 36±1° C. for 48±2 hours. The number of the viable *Bifidobacterium lactis* BL-99 counted in the medium was 3.7×10$^8$ cfu/mL. The stock solution of the culture and a 5-fold concentrated solution were orally gavaged to the mouse subjects at 20.0 mL/kg BW for 3 days, followed by 7 days of observation. Control groups for the stock solution and the 5-fold concentrated solution of the culture were set up in the experiment. The test results suggest that the BBL culture stock and 5-fold concentrate of the *Bifidobacterium lactis* BL-99 had no statistically significant effect on the weight gain of the mice compared with the respective control groups (p>0.05), while no toxic reaction or death of the mouse subjects was observed.

The antibiotic sensitivity of *Bifidobacterium lactis* BL-99 was evaluated with the method of SN/T 1944-2007 "Determination of Bacterial Resistance in Animals and Their Products". The evaluation results show that *Bifidobacterium lactis* BL-99 is sensitive to Ampicillin, Penicillin G, Erythromycin, Chloramphenicol, Clindamycin, Vancomycin, Tetracycline and the like. The requirements of the European Food Safety Authority in the evaluation of drug resistance of edible bacteria are satisfied. *Bifidobacterium lactis* BL-99 does not contain foreign antibiotic resistant genes and is safely edible.

Example 2: Analysis of the Effect of Active *Bifidobacterium lactis* in Regulating the Intestinal Flora This example is intended to verify the effect of the *Bifidobacterium lactis* according to the present invention in intestinal regulation. For the principles and procedures, reference can be made to "Technical Specifications for Health Food Examination and Evaluation: Standards for Intestinal Flora Function Regulation".

After culturing in MRS liquid medium at 37° C. for 16 hours, the *Bifidobacterium lactis* BL-99 strain was centrifuged at 4° C. and 2500 rpm for 10 minutes, and the bacteria were collected, washed with phosphate buffered saline (PBS), and freeze-dried to obtain a bacteria powder which was stored at −18° C. or lower before use in various experiments and studies in this example.

Thirty-six healthy SPF BABL/c mice weighing 18-22 g (supplied by Beijing Huafukang Biotechnology Co., Ltd.) were taken. After 3 days of adaptive feeding, they were randomly divided into 3 groups, each with 12 animals, i.e., a blank control group and a sample group. Each group of animals was gavaged with sterile water having dissolved

*Bifidobacterium lactis* BL-99 powder (gavage volume 0.2 mL/10 g), and the blank control group was gavaged with sterile water of the same volume. The feeding or gavage was done once a day for 14 days consecutively. Gavage volume: $1.3 \times 10^7$ CFU/ml (converted in accordance with an amount of $2 \times 10^9$ CFU/d as needed by human, with a conversion factor between human and mouse of 0.0026). After the adaptive feeding, mouse feces were collected under aseptic conditions into numbered sterile centrifuge tubes, with 2-3 pellets of about 100 mg from each mouse, and transferred to an aseptic operation room under low temperature conditions for flora measurement. At the end of the experiment, mouse feces were collected again. The mice were grouped and numbered with picric acid, weighed on the 8th and 14th days of administration of the test substance, and the gavage volume of the mice was calculated. The mice were weighed once at the end of the experiment. Colony counting: selective media were prepared according to the strain to be identified. The strain to be tested and the corresponding medium are shown in Table 3. Sterilization was carried out followed by uniform shaking, cooling to 45° C.-50° C., and pouring into a plate before use.

TABLE 3

Selective medium used for testing genus/species in the feces

| Genus/Species to be tested | Selective medium |
|---|---|
| *Enterobacter* | Eosin Methylene Blue (EMB) Agar |
| *Enterococcus* | Sodium Azide-Crystal Violet-Aescin Agar |
| *Bifidobacterium* | BBL Agar |
| *Lactobacillus* | LBS Agar |
| *Clostridium perfringens* | Tryptone-Sulfite-Cycloserine (TSC) Agar |

The collected mouse feces were placed in a sterile tube containing 0.5 mL of normal saline, prepared into a bacterial suspension, and shaken for 1 min before use. 0.1 mL of the bacteria suspension was taken with a 0.1 mL micropipette, slowly injected into 0.9 mL of sterile saline, shaken or repeatedly pipetted to mix well to make a 1:10 bacteria suspension. A 10-fold gradient dilution was conducted in the same way to 10 to 7 g/ml by using another 0.1 mL micropipette tip. According to the number of viable bacteria to be identified, two consecutive appropriate dilutions were selected. For each dilution, 10 μL of bacterial suspension was taken by a 10 μL micropipette, surface coated on a plate with the selective agar, and cultured according to the culture conditions shown in Table 4. For the colony counting method, reference can be made to "GB 4789.2-2010 National Food Safety Standard, Food Microbiological Examination: Aerobic Plate Count".

TABLE 4

Medium and culture condition for testing intestinal flora

| Items | Medium | Culture condition |
|---|---|---|
| *Enterobacter* | Eosin Methylene Blue Agar | 24 h culture, 36° C. ± 1° C. |
| *Enterococcus* | Sodium Azide-Crystal Violet-Aescin Agar | 48 h culture, 36° C. ± 1° C. |
| *Bifidobacterium* | BBL Agar | 48 h anaerobic culture, 36° C. ± 1° C. |
| *Lactobacillus* | LBs Agar | 48 h culture, 36° C. ± 1° C. |
| *Clostridium perfringens* | TSC Agar | 24 h anaerobic culture, 36° C. ± 1° C. |

SPSS17.0 was used for data statistics. The changes of *Bifidobacterium, Lactobacillus, Enterococcus*, and Enterobacteria before and after the experiment and between the groups were compared. For the test group, the change before and after the experiment was significant, and the animal test result of the test sample could be determined as positive if any of the following conditions was met: (i) there was a significant increase in *Bifidobacterium* or *Lactobacillus* in feces, a decrease or no significant change in *Clostridium*, no significant change in *Enterococcus* or *Enterobacter*; (ii) there was a significant increase in *Bifidobacterium* or *Lactobacillus* in feces, a decrease or no significant change in *Clostridium*, and a significant increase in *Enterococcus* and *Enterobacter* with the increase being lower than the increase in *Bifidobacterium* or *Lactobacillus*.

The results of the body weight changes of animals during the experiment are shown in Table 5. During the experiment, the animals showed normal characteristics, and no adverse reaction occurred after the administration of the test substance.

TABLE 5

Body weight changes of animals

| Number | Group | Number of animals | Initial weight (g) | Mid-term weight (g) | Final weight (g) |
|---|---|---|---|---|---|
| 1 | Control | 14 | 21.89 ± 1.25 | 22.14 ± 0.87 | 21.24 ± 0.87 |
| 2 | BL-99 | 14 | 23.36 ± 0.77 | 22.41 ± 0.93 | 22.59 ± 1.53 |
| 3 | BB-12 | 14 | 22.31 ± 1.07 | 22.00 ± 1.55 | |

Tables 6 to 10 record the changes of different bacteria in the animal intestine before and after the test. From Table 6 to Table 10, it can be seen that *Bifidobacterium lactis* BL-99 can significantly promote the growth of *Bifidobacterium* and *Lactobacillus*, while having no significant effect on *Enterobacter, Enterococcus*, and *Clostridium perfringens*. According to the "Technical Specifications for Health Food Examination and Evaluation: Standards for Intestinal Flora Function Regulation", it can be concluded that the *Bifidobacterium lactis* BL-99 in this study has the effect of regulating intestinal flora.

TABLE 6

Changes of animal intestinal *Bifidobacterium* before and after the test (LgCFU/g)

| Group | Number of animals | Before intervention | After intervention | p value for in-group comparison before and after intervention | p value for comparison with control after intervention |
|---|---|---|---|---|---|
| Control | 14 | 8.66 ± 0.57 | 8.94 ± 0.46 | 0.196 | 0.000 |
| BL-99 | 14 | 8.32 ± 0.65 | 9.91 ± 0.52** | 0.000 | 0.000 |
| BB-12 | 14 | 8.49 ± 0.85 | 10.18 ± 0.87** | 0.566 | 0.001 |

TABLE 7

Changes of animal intestinal *Lactobacilli* before and after the test (LgCFU/g)

| Group | Number of animals | Before intervention | After intervention | p value for in-group comparison before and after intervention | p value for comparison with control after intervention |
|---|---|---|---|---|---|
| Control | 14 | 8.66 ± 0.57 | 8.94 ± 0.46 | | |
| BL-99 | 14 | 8.32 ± 0.65 | 9.91 ± 0.52** | 0.000 | 0.000 |
| BB-12 | 14 | 8.49 ± 0.85 | 10.18 ± 0.87** | 0.001 | 0.000 |

TABLE 8

Changes of animal intestinal *Enterobacteria* before and after the test (LgCFU/g)

| Group | Number of animals | Before intervention | After intervention | p value for in-group comparison before and after intervention | p value for comparison with control after intervention |
|---|---|---|---|---|---|
| Control | 14 | 6.48 ± 0.32 | 6.98 ± 0.74 | 0.123 | |
| BL-99 | 14 | 6.64 ± 0.49 | 6.63 ± 0.56 | 0.985 | 0.421 |
| BB-12 | 14 | 6.60 ± 0.52 | 6.57 ± 0.71 | 0.875 | 0.193 |

TABLE 9

Changes of animal intestinal *Enterococcus* before and after the test (LgCFU/g)

| Group | Number of animals | Before intervention | After intervention | p value for in-group comparison before and after intervention | p value for comparison with control after intervention |
|---|---|---|---|---|---|
| Control | 14 | 6.62 ± 0.27 | 6.78 ± 0.61 | 0.467 | |
| BL-99 | 14 | 6.25 ± 0.90 | 7.05 ± 0.66 | 0.014* | 0.401 |
| BB-12 | 14 | 6.67 ± 0.22 | 6.71 ± 0.59 | 0.826 | 0.826 |

TABLE 10

Changes of animal intestinal *Clostridium perfringens* before and after the test (LgCFU/g)

| Group | Number of animals | Before intervention | After intervention | p value for in-group comparison before and after intervention | p value for comparison with control after intervention |
|---|---|---|---|---|---|
| Control | 14 | 8.71 ± 0.17 | 9.10 ± 0.49 | 0.060 | |
| BL-99 | 14 | 9.42 ± 0.25 | 9.57 ± 0.53 | 0.286 | 0.219 |
| BB-12 | 14 | 9.23 ± 0.51 | 9.31 ± 0.42 | 0.552 | 0.403 |

Comparison of Intestinal Flora Regulating Effects of Different Doses of Active *Bifidobacterium lactis* and the Inactivated Bacteria The intestinal flora regulating effects of active *Bifidobacterium lactis* and the inactivated bacteria were tested respectively.

Viable bacteria sample: according to the sample specification, 1 g of a viable bacteria sample was weighted and suspended in a PBS solution to 40 ml; namely, the concentration of the viable bacteria was $2.5 \times 10^9$ CFU/ml.

High-dose group: the gavage dose for a 20 g mouse was 0.4 ml as calculated according to a gavage amount of 0.2 ml/10 g in mice, and the gavage dose for the mice in the high-dose group was $10^9$ CFU/20 g.

Medium-dose group: 5 ml of the high-dose suspension was taken and added to PBS to a volume of 50 ml; the gavage dose for a 20 g mouse was 0.4 ml as calculated according to a gavage amount of 0.2 ml/10 g in mice, and the gavage dose for the mice in the medium-dose group was $10^8$ CFU/20 g.

Low-dose group: 5 ml of the medium-dose suspension was taken and added to PBS to a volume of 50 ml; the gavage dose for a 20 g mouse was 0.4 ml as calculated according to a gavage amount of 0.2 ml/10 g in mice, and the gavage dose for the mice in the low-dose group was $10^7$ CFU/20 g.

Non-viable bacteria sample: according to the sample specification, 1 g of viable bacteria sample was weighed and suspended in a PBS solution to 40 ml; namely, the concentration of the viable bacteria was $2.5 \times 10^9$ CFU/ml. The viable bacterial sample at a concentration of $2.5 \times 10^9$ CFU/ml was killed by heating at 100° C. for 20 minutes. The process for the sample setup of the high, medium, and low-dose groups was the same as the above viable bacteria groups.

Six-week-old BABL/c mice were raised in a clean grade animal housing at a temperature of 22° C. and humidity of 10-60%, with 12 hour-lighting alternating between light and darkness, and provided with standard feed and free drinking water. 183 mice was adaptively fed for 5 days and randomly divided into 13 groups with 14 mice in each group. The groups are shown in Table 11.

TABLE 11

Groups in the experiment of intestinal flora regulation

| Group | Test substance | Number of animals | Gavage (Daily intake of human) |
|---|---|---|---|
| Control | PBS | 14 | — |
| Low-dose viable BL-99 | viable BL-99 | 14 | $3.88 \times 10^9$ |
| Medium-dose viable BL-99 | viable BL-99 | 14 | $3.88 \times 10^{10}$ |
| High-dose viable BL-99 | viable BL-99 | 14 | $3.88 \times 10^{11}$ |
| Low-dose non-viable BL-99 | non-viable BL-99 | 14 | $3.88 \times 10^9$ |
| Medium-dose non-viable BL-99 | non-viable BL-99 | 14 | $3.88 \times 10^{10}$ |
| High-dose non-viable BL-99 | non-viable BL-99 | 14 | $3.88 \times 10^{11}$ |

Before the gavage, the feces of each mouse were collected under aseptic conditions, labeled, and stored at −20° C., and the intestinal flora was examined. In the experiment, each test substance was administered according to a gavage amount of 0.2 ml/10 g, and PBS was given to the control group on Day 1 to Day 14. The experimental groups were given the corresponding dose of test substance by gavage according to Table 11. The mice were weighed once a week, and the gavage volume was adjusted according to the body weight. After 14 days, the feces of each mouse were collected under aseptic conditions, labeled, and stored at −20° C., and the intestinal flora was examined.

Before and after the experiment, there was no significant difference in body weight among the mice in each group. At the phylum level, after supplementing of different doses of probiotics, the relative abundance of Firmicutes in the mouse intestinal flora increased while the relative abundance of Bacteroidetes and Proteobacteria decreased. Studies have shown that the ratio of Firmicutes to *Bacteroides* was closely correlated with intestinal diseases in human, and patients with obesity tend to have a lower ratio. However, patients with enteritis and intestinal stress syndrome tend to have a higher abundance of Proteobacteria.

The effect of BL-99 on the intestinal flora at the genus level is shown in Table 12.

TABLE 12

The effect of BL-99 on the intestinal flora

| Genus | Control | Low-dose | Medium-dose | High-dose | Non-viable low-dose | Non-viable medium-dose | Non-viable high-dose |
|---|---|---|---|---|---|---|---|
| *Bacteroides* | 9.8061 ± 2.094 | 5.9873 ± 2.653 | 10.3848 ± 1.7492 | 12.2986 ± 2.0316 | 8.2817 ± 2.4495 | 6.1992 ± 2.2837 | 7.2022 ± 2.4586 |
| *Lactobacillus* | 3.0166 ± 0.4635 | 7.328 ± 2.6521 | 0.455 ± 0.6184 | 0.8324 ± 1.9844 | 0.9849 ± 0.0555 | 2.6327 ± 1.3368 | 1.6724 ± 2.1265 |
| *Desulfovibrio* | 2.1391 ± 0.5097 | 2.4365 ± 1.0559 | 0.4938 ± 0.2063 | 0.7507 ± 0.3162 | 1.0156 ± 0.3670 | 2.2092 ± 2.7254 | 0.9468 ± 0.4183 |
| *Enterobacter* | 0.3447 ± 0.0971 | 0.4023 ± 0.2634 | 0.1529 ± 0.0805 | 0.2402 ± 0.1515 | 0.2063 ± 0.0603 | 0.3967 ± 0.1583 | 0.188 ± 0.0618 |

Data from the probiotic groups show that only low-dose of BL-99 significantly increases the relative abundance of *Lactobacillus* in the mouse intestine at the genus level, as compared to the control group, whereas the abundance increases dose-dependently from low to high. On the other hand, the non-viable high-dose shows a significant inhibitory effect on *Desulfovibrio* and *Enterobacter*.

The inhibitory effect of BL-99 on the pathogenic bacteria *Helicobacter* and *Escherichia-Shigella* is shown in Table 13.

TABLE 13

The inhibitory effect of BL-99 on pathogenic bacteria

| Genus | Control | Low-dose | Medium-dose | High-dose | Non-viable low-dose | Non-viable medium-dose | Non-viable high-dose |
|---|---|---|---|---|---|---|---|
| *Helicobacter* | 0.1254 ± 0.0492 | 0.0528 ± 0.0209 | 0.1614 ± 0.0531 | 0.1174 ± 0.0393 | 0.1919 ± 0.3326 | 0.0536 ± 0.0371 | 0.1292 ± 0.1371 |
| *Escherichia-Shigella* | 0.0281 ± 0.0054 | 0.009 ± 0.0013 | 0.0031 ± 0.0013 | 0.0077 ± 0.0012 | 0.0036 ± 0.0025 | 0.0025 ± 0.0018 | 0.0034 ± 0.0024 |

The analysis of pathogenic bacteria further show that the BL-99 low-dose group has a significant inhibitory effect on *Helicobacter*, while all groups have an inhibitory effect on *Escherichia-Shigella*, with the non-viable bacteria having a better effect.

The above experiments demonstrate that supplementation of BL-99 in the low-dose group can adjust the balance of intestinal flora, promote the growth of beneficial bacteria, inhibit harmful bacteria and even pathogenic bacteria; further, the non-viable bacteria is equally effective, indicating that the supplement of BL-99 in the low-dose group or BL-99 non-viable bacteria can have potential health benefits.

Example 3: Analysis of Immunomodulatory Activity

After culturing in MRS liquid medium at 37° C. for 16 hours, the *Bifidobacterium lactis* BL-99 strain was centrifuged at 4° C. and 2500 rpm for 10 minutes, and the bacteria were collected, washed with phosphate buffered saline (PBS) and freeze-dried, stored below −18° C. before use in various experiments and studies in this example.

Seven-hundred healthy male BALB/C mice, 6-8 weeks old, 16-18 g, provided by Beijing Weitong Lihua Laboratory Animal Technology Co., Ltd., were raised in the Animal Laboratory of the Occupational Hygiene and Poisoning Control Institute of the Chinese Center for Disease Control and Prevention: maintained at room temperature (25±2° C.), relative humidity (55±2)%, 12 h/12 h light-dark cycle, free access to diet and water.

The animals were randomly divided into 5 big panels that were respectively used in different experiments and studies in this example, with 140 mice in each big panel, set up with one normal control group and one dosage group for each probiotic sample in each panel.

The test samples were given to mice by gavage once per day for 28 days with a gavage volume of 0.2 mL/10 g, and the control group was given distilled water by gavage.

According to the probiotic sample information, with reference to the daily human requirement, and based on a conversion factor of the dosage used between a 70 Kg adult human and a 20 g mice, the required dose of each test sample given to mice was calculated. The dose for the BB-12 group was 2.36 mg/kg, and the dose for the BL-99 group was 6.34 mg/kg.

1. Mononuclear-Macrophage Function 1.1 Carbon Clearance Assay

The animals were given samples for 28 consecutive days, weighed, and injected with Indian ink through the tail vein. 2 and 10 minutes after the ink was injected, 20 µL blood was taken and added to a 2M 10.1% sodium carbonate solution, and the OD value was measured at 600 nm. The mice were sacrificed, and the liver and spleen were removed and cleaned off the blood residual on the surface thereof with filter paper, and then weighed.

The phagocytosis index is used to express the ability of mouse carbon clearance, and it is calculated according to the following equation:

$$K = \frac{LgOD1 - LgOD2}{t2 - t1}$$

$$\text{Phagocytosis index} = \frac{\text{Body weight}}{\text{weight of liver} + \text{weight of spleen}} \times \sqrt[3]{K}$$

The phagocytosis index results of the carbon clearance assay are shown in Table 14. The results show that the BL-99 group was lower than the control group and there was no significant difference in the phagocytosis index of the carbon clearance assay between the BB-12 mice and the control group (p>0.05).

TABLE 14

Results of phagocytosis index in the carbon clearance experiment

| Group | Number of animals | phagocytosis index | p value compared with control group |
|---|---|---|---|
| Control | 8 | 7.64 ± 0.62 | — |
| BB-12 | 8 | 7.56 ± 0.61 | 0.902 |
| BL-99 | 9 | 6.43 ± 0.55 | 0.039 |

1.2 Determination of the Organ/Body Weight Ratio

The initial body weight of the mouse and the body weight 28 days after administration were used as the initial body weight and the final body weight, respectively. The mice were sacrificed by dislocation, the spleen and thymus were taken followed by thorough removal of fascia and cleaning off the blood residual on the organs with filter paper, and weighed. The ratio of spleen to weight and the ratio of thymus to weight were calculated.

The results are shown in Table 15. Upon administration of the test sample, compared with the control group, the spleen/weight ratio and thymus/weight ratio of the BL-99 and BB-12 groups were not significantly different from those of the control group. It shows that the BL-99 and BB-12 samples have no effect on the mouse spleen/thymus.

TABLE 15

Changes of organ/body weight ratio in mice

| Group | Number of animals | Spleen/weight ratio (mg/g) | p value | Thymus/weight ratio (mg/g) | p value |
|---|---|---|---|---|---|
| Control | 14 | 13.46 ± 0.56 | — | 10.25 ± 0.61 | — |
| BB-12 | 14 | 13.01 ± 0.52 | 0.100 | 10.22 ± 0.49 | 0.875 |
| BL-99 | 14 | 13.60 ± 0.65 | 0.614 | 10.40 ± 0.36 | 0.418 |

2. Humoral Immunity Assay 2.1 Determination of Serum Hemolysin Half Hemolysis Value ($HC_{50}$)

i. After given the samples for 28 consecutive days, each mouse was immunized by intraperitoneal injection of 0.2 mL SRBC. After 4 days, the eyeballs were removed and the blood was collected in a 1.5 mL centrifuge tube, kept at 4° C. for about 1 hour to allow the serum to be fully precipitated, and centrifuged at 2000 r/min for 10 minutes to collect the serum. The serum was dilute 100 times with SA buffer. The diluted serum was added to a 96-well plate, 100 μL per well, and then 50 μL of 10% (v/v) SRBC and 100 μL complement (diluted with SA solution at 1:8) were added in sequence. The plate was kept in a thermostatic water bath at 37° C. for 30 min, and centrifuged at 1500 r/min for 10 min. Then, 50 μL of the supernatant was taken from the sample wells and the blank control wells respectively, and added to another 96-well culture plate, followed by addition of 150 μL of the Venchi's reagent. Meanwhile, half hemolysis wells were set up by adding 12.5 μL of 10% (v/v) SRBC and subsequently adding the Venchi's reagent to a volume of 200 μL. The plates were shaken well with a shaker and kept for 10 minutes before the optical density of each well was measured with an automatic microplate reader at 540 nm.

ii. The amount of hemolysin is expressed as the half hemolysis value ($HC_{50}$), which is calculated according to the following equation:

iii.

Sample $HC50 = $ $$\frac{\text{Optical density value of the sample}}{\text{Optical density value at } SRBC \text{ half hemolysis}} \times \text{Dilution factor}$$

The results are shown in Table 16. It can be seen from Table 16 that, compared with the control group, the half hemolysis value HC50 of the BL-99 and BB-12 groups both increased (p<0.05), with the BL-99 group higher than the BB-12 group.

TABLE 16

Half hemolysis value $HC_{50}$ results

| Group | Number of animals | $HC_{50}$ | p value |
|---|---|---|---|
| Control | 14 | 51.07 ± 2.17 | — |
| BB-12 | 14 | 66.31 ± 3.66 | 0.000** |
| BL-99 | 14 | 67.43 ± 4.04 | 0.000** |

2.2 Antibody-Producing Cell Detection Assay

The mouse spleen cell suspension immunized with sheep red blood cells (SRBC) was mixed with a certain amount of SRBC. At the presence of complement, the SRBCs around the antibody-secreting spleen cells were dissolved and visible plaques were generated. The number of hemolytic plaques may indicate the number of antibody-producing cells.

After given the samples for 28 consecutive days, each mouse was immunized by intraperitoneal injection of 0.2 mL SRBC. The mice immunized with SRBC for 4 days were sacrificed, and the spleens were taken to prepare a cell suspension of $5 \times 10^6$ cells/mL. After heating and dissolving the agarose, it was mixed with an equal amount of double Hank's solution, and divided into small test tubes, with 0.5 mL per tube, and then 20% (V/V, with physiological saline) 50 μL of packed SRBC and 200 μL of spleen cell suspension was added to the tube and mixed quickly, then poured onto a six-well plate that has been coated with a thin layer of agarose. After the agar was solidified, it was placed in a carbon dioxide incubator and incubated for 1 hour, and then the complement diluted with SA buffer (1:10) was added and the incubation continued for 2 h. The number of hemolytic plaques was counted.

The results of the number of antibody-producing cells are shown in Table 17. Compared with the control group, the BL-99 and BB-12 groups were significantly higher than the control group (p<0.05), with the BL-99 group showing a significant difference as compared to the control group (p>0.05).

TABLE 17

Results of the number of antibody-producing cells

| Group | Number of animals | Number of hemolytic plaques/$10^6$ splenocytes | p value |
|---|---|---|---|
| Control | 11 | 18.64 ± 1.91 | — |
| BB-12 | 10 | 23.30 ± 3.13 | 0.003 |
| BL-99 | 9 | 28.67 ± 2.87 | 0.000 |

3. NK Cell Activity Test 3.1 ConA-Induced Lymphocyte Transformation Assay in Mice After given the samples for 28 consecutive days, the mice were sacrificed. After sterilization in a 75% alcohol beaker, the spleen was taken aseptically, and placed in a small plate having a 3 cm×3 cm four-layer gauze (autoclaved). An appropriate amount of sterile Hank's solution was added, and the spleen was wrapped with the gauze. The spleen was gently grind with an elbow tweezer, and a single cell suspension was prepared, washed twice with Hank's solution, and centrifuged at 1000 rpm for 10 minutes after each wash. Then, the cells were suspended in 2 mL of a complete culture medium, the number of viable cells was counted, and the cell concentration was adjusted to 5×10$^6$ cells/mL. Subsequently, the cell suspension was divided into two wells in a 24-well culture plate with 1 mL per well, and 75 µL of ConA solution (equivalent to 7.5 µg/mL) was added into one well, the other being used as a control, which were kept and incubated at 37° C., 5% $CO_2$ for 72 h. 4 h before the completion of the incubation, the supernatant was gently aspirated from each well, replaced with 0.7 mL of a calf serum-free RPMI 1640 medium, followed by addition of 50 µL/well of MTT (5 mg/mL) and incubation for another 4 h. After the incubation, 1 mL of acidic isopropanol was added to each well and pipetted uniformly to allow the purple crystals to completely dissolve. Then, both were divided in a 96-well culture plate, with each well divided into 2 wells as parallel duplicates, and the optical density value was measured with an enzyme-linked immunoassay at 570 nm wavelength. The proliferation ability of lymphocytes is represented by the optical density value of the well with ConA minus the optical density value of the well without ConA.

The results are shown in Table 18. It can be seen from Table 18 that, compared with the control group, the BB-12 group is significantly higher than the control group (p<0.05), while BL-99 shows no significant change as compared to the control group (p>0.05).

TABLE 18

Results of splenic lymphocyte transformation assay in mice

| Control | Number of animals | OD value with ConA | OD value without ConA | OD difference (δOD) | p value |
|---|---|---|---|---|---|
| BB-12 | 13 | 0.398 ± 0.053 | 0.157 ± 0.035 | 0.241 ± 0.075 | — |
| BL-99 | 13 | 0.542 ± 0.103 | 0.227 ± 0.058 | 0.315 ± 0.097 | 0.024 |

3.2 NK Cell Activity Assay

The animals were given the samples continuously for 28 days. The target cells YAC-1 were subcultured 24 hours before the assay, washed twice with Hank's solution before use, and the cell concentration was adjusted to 1×10$^5$ cells/mL (target cell) with a RPMI1640 complete culture medium containing 10% calf serum. Mice were sacrificed instantly by cervical dislocation. The spleen was taken aseptically and made into skin cell suspension, which was washed twice with Hank's solution, centrifuged at 1000 rpm for 10 min, and resuspended in 2 mL of 10% RPMI 1640 complete medium containing calf serum. Viable cells (the number of live cells should be above 95%) were counted by using Trypan blue, and the cell concentration was adjusted to 1×10$^7$ cells/mL (effector cells) to have an effector-target ratio of 100:1. 100 µL of the target cell and the effector cell each were taken and added to a U-shaped 96-well culture plate. 100 µL of the target cell and the culture medium each were added to the target cell natural release well, and 100 µL of the target cell and 1% NP40 each were added to the target cell maximum release well. Three parallel wells were set up for each of the above. Incubation in a 37° C., 5% CO2 incubator was carried out for 4 hours, and then the 96-well culture plate was centrifuged at 1500 rpm for 5 min. 100 µL of supernatant was drawn from each well and placed in a flat-bottomed 96-well culture plate. At the same time, 100 µL of LDH matrix solution was added and reacted for 3 minutes. Then, 30 µL of 1 mol/L HCL solution was added to each well to quench the reaction, and the OD value at 490 nm was measured on a microplate reader. NK activity is calculated as follows:

$$NK \text{ cell activity } (\%) = \frac{\text{Reaction well } OD - \text{Natural release well } OD}{\text{Maximum release well } OD - \text{Natural release well } OD} \times 100\%$$

The results are shown in Table 19. It can be seen from Table 19 that the NK cell activity of BL-99 is higher than that of the control group and BB-12, and the difference is significant.

TABLE 19

NK cell activity results

| Group | Number of animals | Cell activity (%) | p value |
|---|---|---|---|
| Control | 14 | 30.70 ± 3.31 | — |
| BB-12 | 14 | 33.38 ± 4.17 | 0.078 |
| BL-99 | 14 | 47.92 ± 5.63 | 0.000 |

4. Cellular Immune Response 4.1 Delayed Allergy

After given the sample for 28 consecutive days, each mouse was intraperitoneally injected with 0.2 mL of 2% packed SRBC (v/v, prepared with saline). 4 days after sensitization, the thickness of the left hind toe was measured, with measurements taken at the same site for 3 times and averaged. Then, 20 µL of 20% SRBC was injected subcutaneously at the measurement site. The thickness of the left hind toe was measured 24 hours after the injection, with measurements taken at the same site for 3 times and averaged. The difference in toe thickness (toe swelling) before and after the challenge was used to express the DTH degree.

The results are shown in Table 20. It can be seen from table 20 that before the SRBC challenge, the toe thickness of the mice in each group was at the same level. After overall 24 hours of SRBC challenge, the toes of the mice appeared swelling. The degree of swelling was represented by the difference in the thickness of the toes before and after the challenge. Upon statistical analysis, it was found that, compared with the control group, the BB-12 and BL-99 groups were significantly higher than the control group (p<0.05).

TABLE 20

Results of toe swelling in mice with delayed allergy

| Group | Number of animals | Before injection (mm) | 24 h after injection (mm) | Difference (mm) | p value |
|---|---|---|---|---|---|
| Control | 12 | 1.26 ± 0.06 | 1.65 ± 0.12 | 0.38 ± 0.09 | — |
| BB-12 | 14 | 1.23 ± 0.07 | 1.77 ± 0.10 | 0.50 ± 0.05 | 0.005 |
| BL-99 | 14 | 1.18 ± 0.06 | 1.80 ± 0.12 | 0.62 ± 0.10 | 0.000 |

4.2 Peritoneal Macrophage Phagocytosis Assay in Mouse

After given the sample for 28 consecutive days, and 4 days before the completion of the gavage, each mouse was intraperitoneally injected with 0.2 mL of 2% SRBC to activate the mouse macrophages. On the day of the assay, the mice were sacrificed by cervical dislocation, and 3 mL of Hank's solution with calf serum was injected into the abdominal cavity. The abdomen was gently rubbed 20 times to fully wash out the peritoneal macrophages, a small opening was then cut in the abdominal wall, and 0.5 mL of the peritoneal lavage mixture was drawn and added to the agar ring on a slide, followed by incubation in the incubator at 37° C. for 15-20 min. After the incubation, the non-adherent cells were quickly washed away with normal saline, fixed in methanol for 1 min, and Giemsa stained for 15 min. After rinsing with distilled water and drying, the phagocytosis rate and phagocytosis index was counted under a 40× microscope. The phagocytosis rate is the percentage of phagocytic cells that phagocytize chicken red blood cells per 100 phagocytes; the phagocytosis index is the average number of chicken red blood cells phagocytized by each phagocytic cell. The result is calculated as follows:

$$\text{Phagocytosis percentage (\%)} = \frac{\text{Number of macrophages that phagocytized fluorescent microspheres}}{\text{Number of macrophages counted}} \times 100$$

The results are shown in Table 21. As seen from the results of the phagocytosis rate and phagocytosis index of phagocytes, the phagocytosis rate and phagocytosis index of the BB-12 group did not differ from those of the control group, i.e., the BB-12 group gave negative results in the macrophage phagocytosis assay; both the phagocytosis rate and the phagocytosis index of the BL-99 group were higher than that of the control group, i.e., the BL-99 group gave positive results in the macrophage phagocytosis assay.

TABLE 21

Results of macrophage phagocytosis rate and phagocytosis index

| Group | Number of animals | Phagocytosis rate (%) | p value | Phagocytosis index | p value |
|---|---|---|---|---|---|
| Control | 14 | 22.55 ± 1.58 | — | 0.42 ± 0.04 | — |
| BB-12 | 14 | 22.28 ± 2.75 | 0.799 | 0.47 ± 0.04 | 0.055 |
| BL-99 | 14 | 25.48 ± 2.86 | 0.005 | 0.53 ± 0.04 | 0.000 |

The above results confirm that the isolated *Bifidobacterium lactis* BL-99 strain according to the present invention can improve the immune organ index of the body, non-specific immune function and specific immune function characteristics, thereby improving the immune activity of the body.

Example 4: Analysis of the Efficacy in Prevention and Treatment of Osteoporosis

1. Rat Model of Osteoporosis Using Ovariectomized (OVX) and Probiotic Intervention After culturing in MRS liquid medium at 37° C. for 16 hours, the *Bifidobacterium lactis* BL-99 strain was centrifuged at 4° C. and 2500 rpm for 10 minutes, and the cells were collected, washed with phosphate buffered saline (PBS) and freeze-dried, and stored below −18° C. for use in the experiments and studies of Example 2 to Example 5 of the present invention.

Eighty-five female adult SD rats, 17-week-old, weighing 200-300 g were randomly divided into 3 groups with 10 rats in each group. Twenty rats underwent ovariectomy (OVX), and the remaining 10 rats underwent sham operation. The rats were under 12 h light/darkness every day, at room temperature of about 25° C., and had free access to water. After 12 weeks of surgical intervention, animals in the model observation group were sacrificed, samples of uterus, femur, and tibia were collected, and osteoporosis-related indexes, such as uterine coefficient, bone microstructure morphology, and bone structure model parameters, were measured.

After the animals rested for two weeks, the test substance was administered by gavage for a course of treatment of once per day for 12 consecutive weeks. The OVX rats were fed BL-99 probiotics, and the sham operation group and the OVX blank control group were fed distilled water; the specific administration of the animals was as follows. The specific grouping of animals is shown in Table 22.

TABLE 22

Groups in the OVX experiment

| No. | Group | Number of animals | Probiotic dosage |
|---|---|---|---|
| 1 | Sham control | 10 | Saline |
| 2 | OVX control | 10 | Saline |
| 3 | OVX + BL-99 | 10 | Saline + 10$^9$ CFU/mL |

The body weight changes of the animals before and after the intervention are shown in FIG. 1A. After the model was successfully established, the weight of the sham operation group was significantly lower than the rest OVX groups, consistent with the significant increase in weight of post-menopausal women. The body weight in each intervention group increased to a certain extent over the 12-week intervention period. There was no significant difference in body weight between the OVX blank group and the OVX+BL-99 intervention group before and after intervention.

After 12 weeks of intervention, the animals were sacrificed, the uterus was collected, weighed, and recorded, and the uterine coefficient (i.e., the ratio of the weight of the uterus to the body weight) was calculated. The experimental results (FIG. 1B) show a remarkably significant difference between the uterine coefficient of the OVX group and that of the sham operation group (p<0.001, vs. sham operation), indicating that the uterus significantly shrunk after ovariectomy as the in vivo estrogen decreased. However, the OVX control group and the OVX+BL-99 intervention group had no effect on the weight of the uterus, indicating no estrogen-like side effects.

2. Bone Tissue Morphometric Measurement

A longitudinal cut were made along the sagittal plane at proximal ⅓ of the left tibia, and a specimen of about 1×0.5×0.5 cm$^3$ was obtained and soaked in a decalcification solution of 10% EDTA/PBS (pH 7.4) for about 1 week until complete decalcification, with the solution changed every 3 days. Then, the specimen was routinely dehydrated, embed in paraffin, cut along the sagittal plane (thickness 4 μm), and HE stained. The total tissue area, trabecular bone area, and total trabecular bone circumference were determined with a pathological image analyzer, and the percentage of trabecular bone area, the number of trabecular bone, the thickness of trabecular bone, and the degree of trabecular separation were calculated by conversion with calculation equations. The appearance, arrangement, and structural integrity of the trabecular bone of bone tissue section were also examined.

Figure 2D:
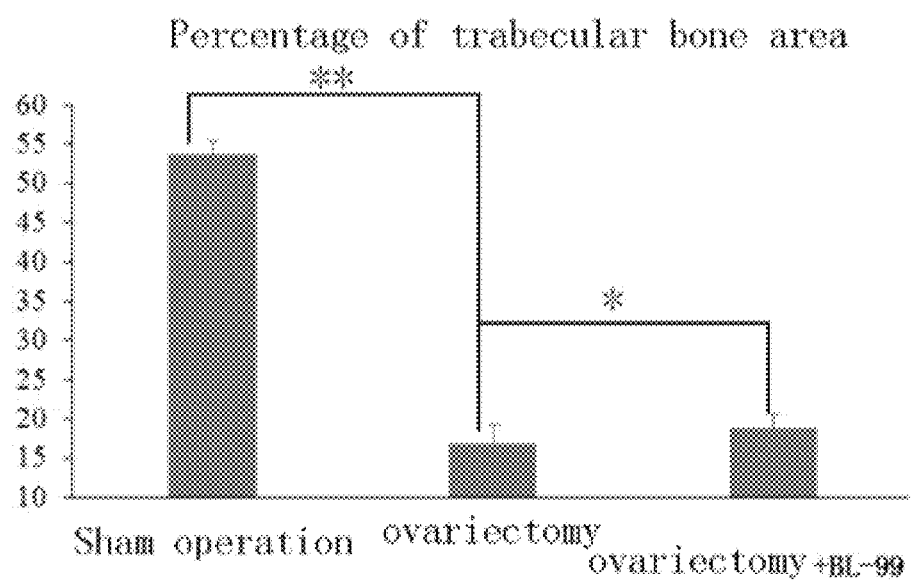
FIG. 2D shows the changes in the percentage of trabecular bone area before and after the *Bifidobacterium lactis* BL-99 intervention in Example 4.

After 12 weeks of intervention with BL-99, the HE staining results (FIGS. 2A-2C) show that the trabecula of the sham operation group was tightly arranged and the structure was complete; whereas, the trabecula of the OVX control group was loosely arranged and the structure was incomplete, and the percentage of trabecular bone area was significantly reduced as compared to the sham operation group ($p<0.001$, vs. sham operation). Compared with the OVX control group, the BL-99 group was able to increase the percentage of trabecular bone area by about 12.5% (OVX: 16.8±2.5%, OVX+BL-99: 18.9±1.8) ($p<0.05$, vs. OVX) (FIG. 2D), suggesting the ability of the BL-99 of inhibiting bone loss caused by estrogen deficiency and a certain protective effect on bone.

Figure 3D:
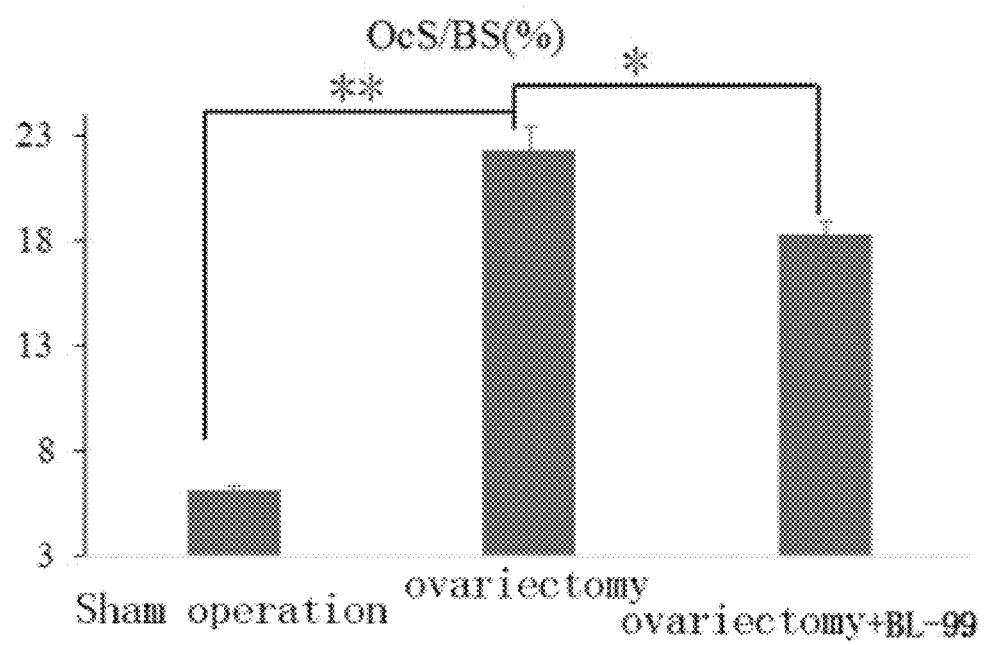
FIG. 3D shows the changes in the percentage of osteoclasts in the bone surface (OcS/BS) before and after the *Bifidobacterium lactis* BL-99 intervention in Example 4.
Figures 4A, 4B:
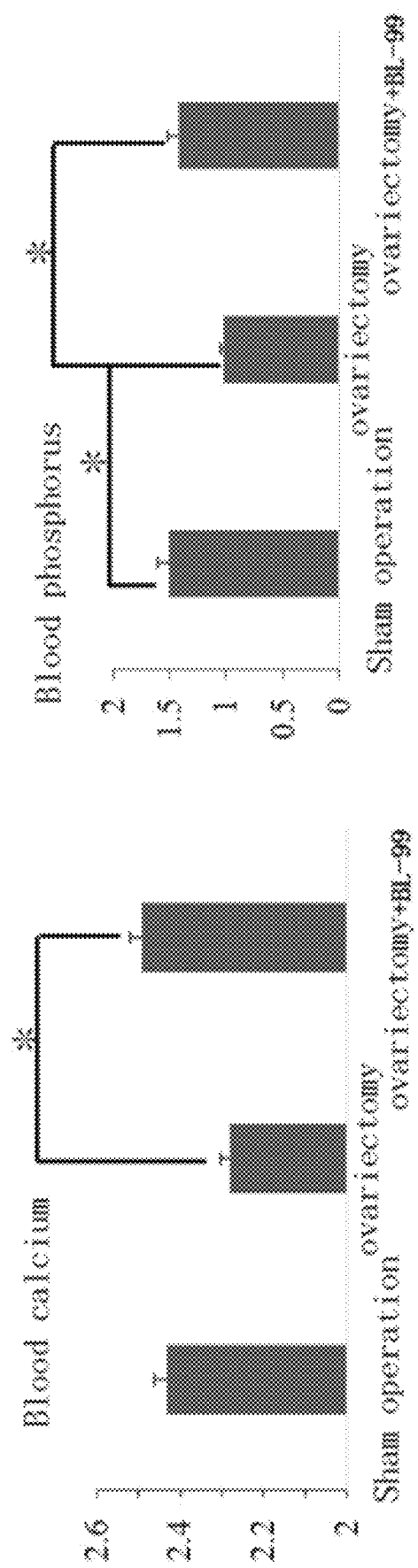
FIGS. 4A to 4D show the changes in blood calcium, blood phosphorus, serum osteocalcin, and type I-collagen C-terminal peptide after the *Bifidobacterium lactis* BL-99 intervention.
Figures 4C, 4D:
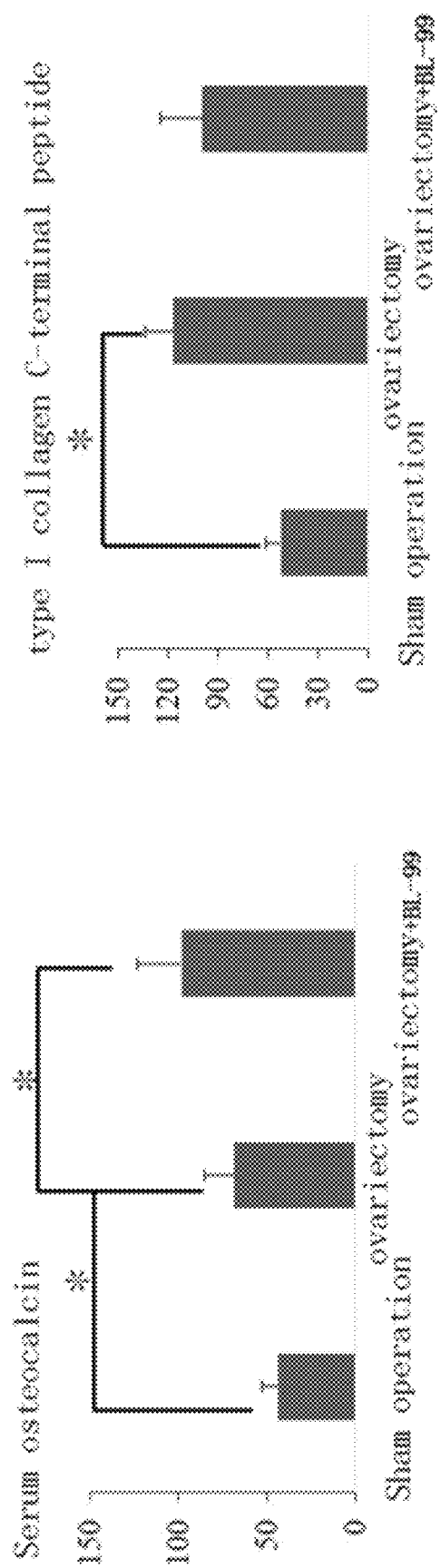
Figures 5A, 5B:
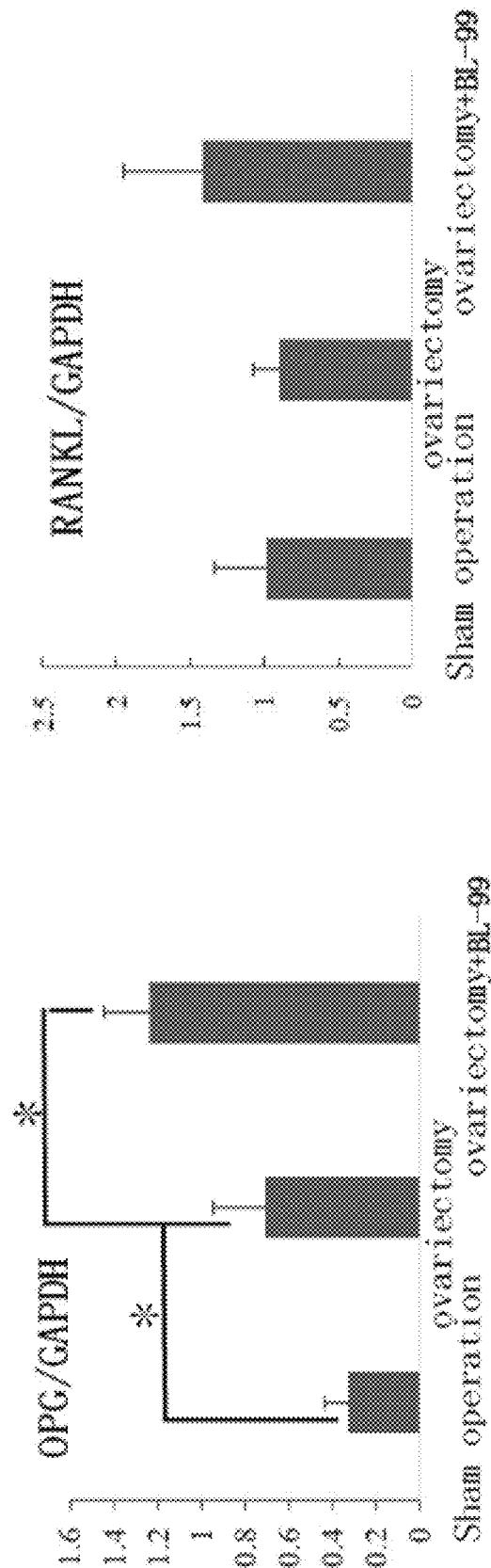
FIGS. 5A to 5E show the effect of *Bifidobacterium lactis* BL-99 intervention on the regulation of bone anabolism-related genes.
Figures 5C, 5D:
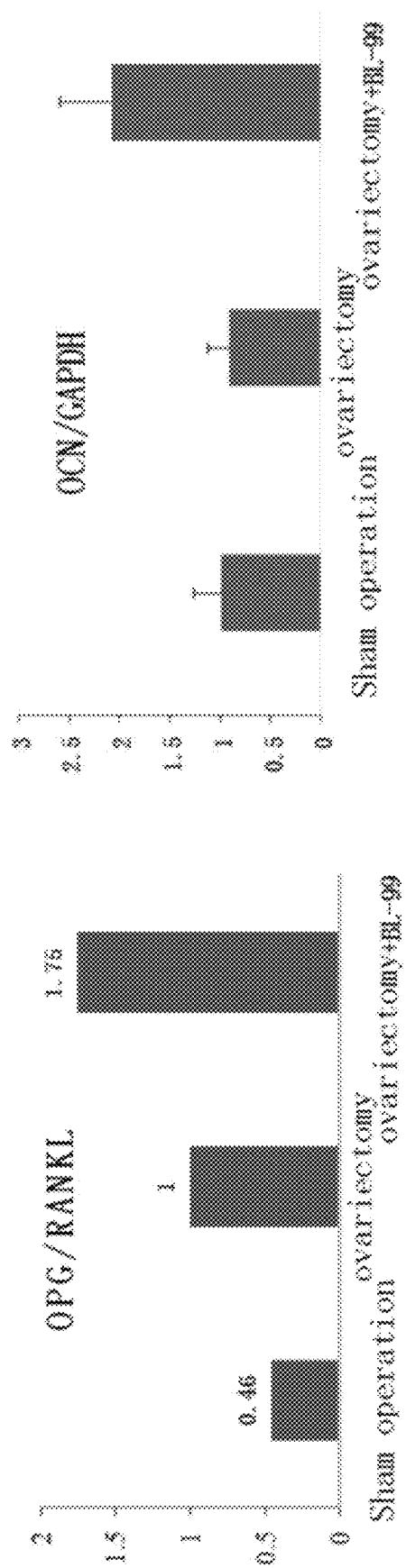
Figure 5E:
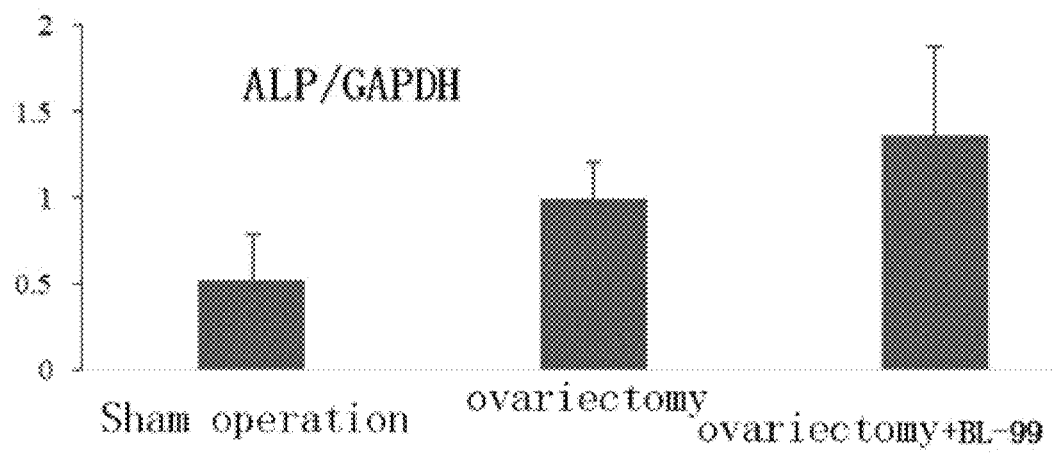

Osteoclasts are the primary cells responsible for bone resorption in the body and play an important role in bone development, growth, repair and reconstruction. Derived from the mononuclear-macrophage system, osteoclasts is a special terminally differentiated cell and can form huge multinucleate cells from the monocyte precursor cells thereof through cell fusion. Osteoclasts function correspondingly to osteoblasts, and they work synergistically and play an important role in the development and formation of bones. Highly expressed tartrate resistant acid phosphatase (TRAP) is one of the main markers of osteoclasts. The results of TRAP staining of tibia are shown in FIGS. 3A-3C. A positive staining results in the cytoplasm of osteoclasts located in the bone being stained in a burgundy color. The number of TRAP stained osteoclasts on the tibia surface of the OVX control group was significantly higher than that of the sham operation group. Compared with rats in the OVX control group, the number of TRAP stained osteoclasts in the BL-99 group was significantly reduced by about 17.9% (OVX: 22.3±1.1%, OVX+BL-99: 18.3±0.6) ($p<0.05$, vs. OVX). Estrogen can inhibit the activity of osteoclasts in vivo and induce the apoptosis of osteoclasts to function in anti-bone resorption. In OVX animals, due to the significantly lower estrogen level, the inhibitory effect thereof on osteoclasts was absent, and the number of osteoclasts and the bone resorption capacity increased significantly (FIG. 3D), which eventually leads to a significant reduction in cancellous bone mass. Further, the results from FIGS. 2A-2D and, FIGS. 3A-3D suggest that BL-99 intervention can inhibit the loss of bone mass caused by OVX, possibly by reducing the number of osteoclasts.

3. Measurement of Biochemical Indicators

The biochemical indicators measured include blood calcium, blood phosphorus, serum osteocalcin (OCN), and type I collagen C-terminal peptides (CTX-I). Atomic absorption spectrophotometry was used to determine blood calcium and blood phosphorus, and serum samples were used directly for measurement. The kits used in the tests included: Calcium LiquiColor Test (REF 0155-225), Phosphorus Liqui-UV Test (REF 0830-125), both manufactured by the Stanbio Laboratory (NorthMainBoerne, FX, USA). As shown in FIGS. 4A to 4D, compared with the sham operation group, the blood calcium and blood phosphorus levels of the OVX blank group decreased, though the decrease in blood calcium was not statistically significant. Nevertheless, compared with the OVX control group, the BL-99 intervention group was able to significantly elevate serum calcium ions (OVX: 2.28±0.02 mg/dl, OVX+BL-99: 2.49±0.03 mg/dl), with an increase by about 10%, and phosphorus ions (OVX: 1.02±0.08 mg/dl, OVX+BL-99: 1.41±0.11 mg/dl), with an increase by about 40%.

Serum osteocalcin is an active polypeptide secreted by osteoblasts and plays an important role in regulating bone metabolism, the level of which reflects the activity of osteoblasts. Type I collagen C-terminal peptide is a small fragment after degradation of type I collagen, and the bone resorption condition may be assessed by the content and change thereof. Serum osteocalcin and type I collagen C-terminal peptide were measured by using an enzyme-linked immunosorbent assay (ELISA) kit, and the procedure of the measurement was carried out in accordance with the instructions in the kit. The kits used in the tests were: Rat Osteocalcin ELISA Kit, Rat C-telopeptide of Collagen alpha-1(I) chain ELISA Kit, both manufactured by SAB (SABiosciences, USA).

As shown in FIGS. 4A to 4D, compared with the OVX control group, the BL-99 intervention group was able to significantly increase the serum osteocalcin level by about 44.6% (OVX: 68.6±16.4 pg/dl, OVX+BL-99: 92.6±24.3 pg/dl) and reduce the serum level of type I collagen C-terminal peptide by about 14.6%, though not statistically significant.

4. PCR Assay of Bone Specimen

In this example, investigation was extended to a gene expression assay related to osteoclast formation and osteoblast formation in a bone specimen. The intervention method of BL-99 was as that in the above section "1. Rat model of osteoporosis using ovariectomized (OVX) and probiotic intervention".

After extraction of total RNA from the bone tissue using Trizol, RNA was reversely transcript into cDNA by using a reverse transcription kit, and PCR amplification was then performed with different gene primers (see Table 23).

TABLE 23

Primer used for gene expression analysis.

| Primer | Accession No. | Sequence (5'-3') | Tm, °C. |
|---|---|---|---|
| ALP | NM_013059 | F: GCAAGGACATCGCCTATCAG (SEQ ID No. 2) | 53 |
| | | R: AGTTCAGTGCGGTTCCAGAC (SEQ ID No. 3) | |

TABLE 23-continued

Primer used for gene expression analysis.

| Primer | Accession No. | Sequence (5'-3') | Tm, °C. |
|---|---|---|---|
| OCN | Nm_013414 | F: CACAGGGAGGTGTGTGAG (SEQ ID No. 4)<br>R: TGTGCCGTCCATACTTTC (SEQ ID No. 5) | 56 |
| OPG | NM_012870 | F: GTTCTTGCACAGCTTCACCA (SEQ ID No. 6)<br>R: AAACAGCCCAGTGACCATTC (SEQ ID No. 7) | 55 |
| RANKI | NM_057149 | F: CATCGGGTTCCCATAAAGTC SEQ ID No. 8)<br>R: CTGAAGCAAATGTTGGCGTA (SEQ ID No. 9) | 55 |
| GAPDH | NM_017008 | F: AGTCTACTGGCGTCTTCAC (SEQ ID No. 10)<br>R: TCATATTTCTCGTGGTTCAC (SEQ ID No. 11) | 55 |

Compared with the OVX control group, the BL-99 intervention group was able to significantly increase the gene expression of osteoprotegerin (OPG) but not significantly affect the gene expression of RANKL, thereby increasing the OPG/RANKL ratio. RANKL binds to the RANK receptor on the surface of osteoclasts to promote the differentiation and activation of osteoclasts and inhibit their apoptosis; osteoprotegerin OPG prevents the binding of RANKL to RANK, thereby preventing the activation of osteoclasts, inhibiting the function of osteoclasts and reducing bone resorption, which plays a negative regulatory role. The ratio of OPG/RANKL indicates the regulation level of osteoclasts in vivo. It was found in this study that the OPG/RANKL gene expression ratio increased after the intervention of BL-99 from 1 (the OVX control group) to 1.75, with an increase in the ratio of about 75%. This result suggests that BL-99 had a significant effect in inhibiting osteoclast formation. In addition, as shown in FIGS. 5A to 5E: compared with the OVX control group, the BL-99 intervention group was able to increase osteocalcin by about 1.1 times (OVX: 0.908±0.107, OVX+BL-99: 2.075±0.643) and increase the gene expression level of alkaline phosphatase by about 37.8% (OVX: 0.990±0.217, OVX+BL-99: 1.364±0.513). The expression level of these two genes is closely related to the ability of bone formation. Therefore, BL-99 intervention can promote the formation of new bones by promoting the expression of osteogenesis-related genes and antagonize the loss of bone mass caused by OVX.

The results in the above study confirm that the *Bifidobacterium lactis* BL-99 according to the present invention can significantly inhibit the loss of bone mass caused by ovariectomy or low estrogen, and increase blood calcium and blood phosphorus.

Example 5: Preparation of BL-99 Bacteria Powder and its Use in Food Production

Figure 6:
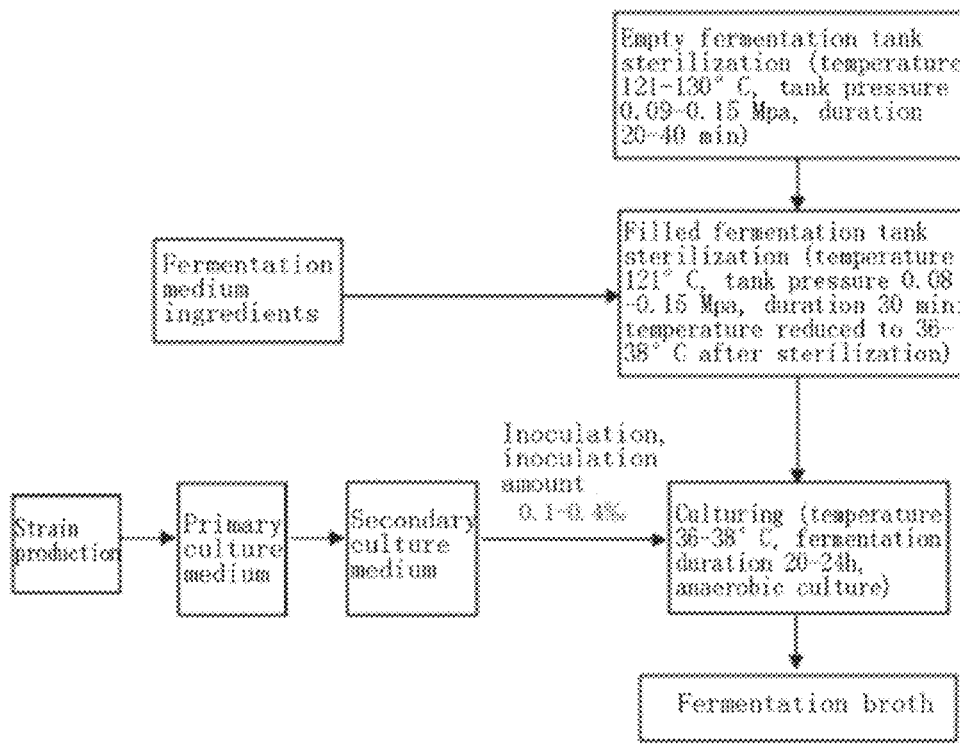
FIG. 6 is a schematic diagram of a fermentation process in a specific example of the present invention.

With reference to the fermentation process shown in FIG. 6, the *Bifidobacterium lactis* BL-99 (i.e., *Bifidobacterium lactis* with the deposit number of CGMCC No. 15650) provided by the present invention was anaerobically cultured in a TPY liquid medium. TPY liquid medium (g/L): hydrolyzed casein 10.0, soy peptone 5.0, yeast powder 2.0, glucose 5.0, L-cysteine 0.5, dipotassium phosphate 2.0, magnesium chloride 0.5, zinc sulfate 0.25, calcium chloride 0.15, ferric chloride 0.0001, Tween 80 1.0, pH 6.5±0.1. The fermentation broth underwent primary, secondary, and expanded culturing was centrifuged at 4° C. and 2500 rpm for 10 minutes, and the bacteria were collected, freeze-dried to obtain a BL-99 bacteria powder, which was stored at or below −18° C.

The BL-99 bacteria powder prepared in this example can be used for food, feed, or medical purposes. The food may be, for example, a normal food or a health food such as fermented milk, cheese, a dairy beverage, a solid beverage, and milk powder. Preferably, the recommended dose of *Bifidobacterium lactis* BL-99 for human use may be $1.0 \times 10^3$ CFU to $1.0 \times 10^{10}$ CFU/kg body weight/day, more preferably $1.0 \times 10^4$ CFU to $1.0 \times 10^9$ CFU/kg body weight/day in such foods. Alternatively, the recommended dose of *Bifidobacterium lactis* BL-99 for human use may be 0.001 μg to 100 mg/kg body weight/day, more preferably 0.01 μg to 10 mg/kg body weight/day, and still more preferably 0.01 μg to 1 mg/kg body weight/day.

The invention claimed is:

1. A method for improving the immune activity of the body, comprising administering an effective amount of a *Bifidobacterium lactis* strain BL-99 having a deposit number of CGMCC No. 15650 to a subject in need of improving the immune activity of the body.

2. The method according to claim 1, wherein the *Bifidobacterium lactis* strain is in a freeze-dried form.

3. The method according to claim 1, wherein the *Bifidobacterium lactis* strain has a survival rate of viable bacteria of 62% or more when treated in gastric acid at pH 2.5 for 30 minutes, and a survival rate of viable bacteria of 61% or more when treated for 2 hours.

4. The method according to claim 1, wherein improving the immune activity of the body includes increasing the carbon clearance index of the body.

5. The method according to claim 1, wherein improving the immune activity of the body includes increasing the half hemolysis value of the body.

6. The method according to claim 1, wherein improving the immune activity of the body includes increasing the antibody-producing cell number of the body.

7. The method according to claim 1, wherein improving the immune activity of the body includes activating the NK cell activity of the body.

8. The method according to claim 1, wherein improving the immune activity of the body includes increasing the phagocytosis rate and phagocytosis index of macrophages in the body.

9. A method for improving the immune activity of the body, comprising administering an effective amount of a bacteria preparation of *Bifidobacterium lactis* to a subject in need of improving the immune activity of the body, wherein the bacteria preparation comprises a *Bifidobacterium lactis* strain BL-99 having a deposit number of CGMCC No. 15650.

10. The method according to claim 9, wherein the bacteria preparation is a solid bacteria powder in a viable bacteria form or an inactivated form, or a liquid bacteria preparation in a viable bacteria form or an inactivated form.

11. The method according to claim 9, wherein improving the immune activity of the body includes increasing the carbon clearance index of the body.

12. The method according to claim 9, wherein improving the immune activity of the body includes increasing the half hemolysis value of the body.

13. The method according to claim 9, wherein improving the immune activity of the body includes increasing the antibody-producing cell number of the body.

14. The method according to claim 9, wherein improving the immune activity of the body includes activating the NK cell activity of the body.

15. The method according to claim 9, wherein improving the immune activity of the body includes increasing the phagocytosis rate and phagocytosis index of macrophages in the body.

* * * * *